(12) United States Patent
Kelley

(10) Patent No.: US 10,166,106 B2
(45) Date of Patent: *Jan. 1, 2019

(54) METHODS AND DEVICES FOR A SURGICAL HIP REPLACEMENT PROCEDURE

(71) Applicant: Scott Kelley, Chapel Hill, NC (US)

(72) Inventor: Scott Kelley, Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/609,324

(22) Filed: May 31, 2017

(65) Prior Publication Data

US 2018/0000597 A1   Jan. 4, 2018

Related U.S. Application Data

(63) Continuation of application No. 14/829,009, filed on Aug. 18, 2015, now Pat. No. 9,668,867, which is a continuation of application No. 13/671,357, filed on Nov. 7, 2012, now Pat. No. 9,114,014.

(51) Int. Cl.
| | |
|---|---|
| *A61F 2/32* | (2006.01) |
| *A61B 17/16* | (2006.01) |
| *A61F 2/36* | (2006.01) |
| *A61F 2/46* | (2006.01) |

(52) U.S. Cl.
CPC .............. *A61F 2/36* (2013.01); *A61B 17/164* (2013.01); *A61B 17/1659* (2013.01); *A61B 17/1668* (2013.01); *A61F 2/32* (2013.01); *A61F 2/4657* (2013.01); *A61F 2/4684* (2013.01); *A61F 2002/4658* (2013.01); *A61F 2002/4666* (2013.01); *A61F 2002/4668* (2013.01)

(58) Field of Classification Search
CPC ... A61B 5/4528; A61B 17/155; A61B 5/4504; A61B 17/1668; A61B 5/6878; A61B 17/17; A61B 2019/462; A61B 17/3468; A61F 2/3859; A61F 2/36; A61F 2/4684; A61F 2002/30112; A61F 2002/3096; A61F 2/32; A61F 2002/30327; A61F 2002/30331; A61F 2/30
See application file for complete search history.

(56) References Cited

U.S. PATENT DOCUMENTS

| | | | | |
|---|---|---|---|---|
| 9,668,867 | B2* | 6/2017 | Kelley | ...................... A61F 2/36 |
| 2011/0112540 | A1* | 5/2011 | McLean | ............... A61B 17/164 |
| | | | | 606/80 |

* cited by examiner

*Primary Examiner* — Ann Schillinger
(74) *Attorney, Agent, or Firm* — Coats and Bennett, PLLC

(57) ABSTRACT

Devices and methods for use in a hip replacement surgical procedure. One aspect includes methods and devices for reaming selective regions of the femoral canal. This may include reaming distal and proximal sections of the femoral canal prior to reaming a middle region of the canal. Another aspect includes a dummy implant and methods of use. The dummy implant is inserted into the femoral canal and may be used for one or more of retraction of the femur, gauging a space with the acetabulum, and further revising the femoral cut. The aspects may be used together in a single surgical procedure or separately in different surgical procedures.

10 Claims, 21 Drawing Sheets

METHODS AND DEVICES FOR A SURGICAL HIP REPLACEMENT PROCEDURE

CROSS REFERENCE TO RELATED APPLICATIONS

The present application is a continuation of application Ser. No. 14/829,009, filed Aug. 18, 2015 entitled "Methods and Devices for a Surgical Hip Replacement Procedure", which is a continuation of Ser. No. 13/671,357, filed Nov. 7, 2012, now U.S. Pat. No. 9,114,014 entitled "Methods and Devices for a Surgical Hip Replacement Procedure". Each of the '009 and '357 applications is incorporated herein by reference in its entirety.

BACKGROUND

The present application is directed to hip replacement procedures and, more particularly, to methods and devices for preparing and sizing the femur to receive a femoral component.

Hip replacement procedures involve the replacement of the hip joint formed by the head of the femur and the acetabulum of the pelvic bone. Hip replacement procedures include the preparation of the femur for receipt of a first component and preparation of the acetabulum to receive a second component. The two components engage together to replace the hip joint. Numerous surgical approaches exist exposing the joint to perform hip replacement surgeries.

Initially, the transtrochanteric approach was most popular, as advocated by the father of hip replacement surgery, John Charnely. This involved exposing the boney prominence to the side of the human hip, that is attached to the femur and to which the abductor muscles attach, to stabilize the hip/pelvis during gait. Over time, surgeons began going either in front of (anterior orientated approaches) or behind (posterior based approaches) the trochanter.

Anterior orientated approaches had many variations and names (Anteriolateral, Watson-Jones, direct lateral, Smith-Peterson, direct anterior) many of which involved detaching the abductor muscle without removing the trochanter. These approaches all shared a low postoperative hip dislocation rate. However, the most popular of these approaches anterior the trochanter had the drawback of longer recovery and potentially weakened abductor muscle. Posterior orientated approaches were less destructive to the abductor muscle, but with the disadvantage of a higher postoperative dislocation rate.

The ideal approach would have the advantages of approaches anterior to the trochanter in regard to dislocation, without the disadvantages of increased muscle damage/recovery/weakness.

The damage to the soft tissue and muscles with anterior based approaches occurs during the preparation of the femur for the femoral component. The use of cement to obtain implant fixation has largely been replaced by cementless (bone ingrowth) implant designs, that require the intramedulary femoral canal to be reamed and/or rasped to an exact silhouette of the final prosthetic implant. Reamer-based systems have the advantage of accurately machining bone of varying density, similar to the accuracy of a drilling a pilot hole for a screw. The disadvantage of reamers is that occasionally more bone/soft tissue gets reamed than intended. These elongated reamers include cutting edges that extend along their length. The cutting edges extend outward beyond the canal and may contact against the nearby tissue during rotation of the reamer. This contact damages the tissue thus causing a more invasive procedure with additional recovery time for the patient.

As muscle sparing approaches (anterior to the trochanter) have developed, shorter stems that do not require bone preparation using full length straight reamers have been introduced. Techniques that require specific untested implant designs are at risk for unforeseen complications. For rasp prepared short stem implants the risk is for prosthetic subsidence and/or periprosthetic fracture.

A technical consideration, shared by all surgical approaches, involves the sizing and placement of both prosthetic components. In regard to the femoral component, correct size directly affects the depth the component can be seated into the bone. Placed too deep and the leg ends up being left short, but more commonly, placing the component proud, leads to lengthening of the leg. Another drawback of posterior based approaches is the need to place the component proud to obtain adequate hip stability.

While success has been obtained with many different femoral component designs, the most successful and popular implant designs involve the use of rigid tapered reamer preparation. Reamer design initially involved reamers with parallel surface, but now are more popularly designed with a slight taper (3 degree) that is an identical match to the taper design in the femoral implant. This creates an ice cream cone shape to the reamed femur to which an ice cream shape implant is inserted.

To summarize, the potential problems with straight (full length) reaming systems include the following:

1. Difficulty in correctly sizing the canal for receipt of the femoral component. Progressively larger reamers are inserted in the canal as part of the sizing process. Resistance to reaming is a major determinant of when to stop increasing the diameter of the reamer (and subsequently the femoral component size). When using full length reamers, often it isn't possible to determine if the resistance is occurring at the tip, middle or top of the reamer.
2. When the reamers are tapered, the surgeon needs to simultaneously determine not only when the reamer engages cortical bone (correctly sized), but also to what depth the reamer is inserted.
3. Incorrectly reaming too deep requires correction by increasing the size of the femoral component, sometimes to a size larger than desirable.
4. Incorrectly reaming too shallow, if uncorrected, can over-lengthen an extremity.

While the majority of cases are correctly reamed, based on preoperatively templating and surgical experience, the outliers resulting in repeating surgical steps, resulting in either error, prolonged surgical time and/or increased surgical trauma. It is for this reason, surgeons transitioning to muscle sparing approaches anterior to the trochanter, have circumvented the disadvantages of full length reamers, by using shorter rasp based systems. As these implants evolve to shorter length, new challenges and complications are potentially introduced. Rasp based systems have unique sizing challenges and have been associated with higher periprosthetic fracture rates, both intra and postoperatively. Additionally, shorter stems have potentially less stability and surface area for bone attachment and ingrowth, and subsequently painful implants requiring revision.

Therefore, there is a need for a hip replacement procedure that allows surgeons using long stem, reamer based systems to continue transition to muscle sparing approaches, based anterior to the trochanter, without having to experiment with new shorter stem designs. The technique should include methods and devices for sizing the femur, depth of placement and receipt of the femoral component without increased damage to nearby tissue and abductor muscle.

SUMMARY

This patent application is based upon the following beliefs:
1. Tapered reamer systems have advantages over short stemmed rasp based systems.
2. Muscle sparing approaches, anterior to trochanter have the advantages of lower dislocation rates, without disadvantages related to abductor muscle trauma.
3. The disadvantages of reamer based systems can be circumvented by not using long reamers with cutting teeth along the full length and instead breaking the reaming into three parts; distal, proximal and finally middle region.
4. It is the distal reaming that best determines prosthetic implant size.
5. It is the proximal reaming, combined with rasping, that is responsible for the majority of ingrowth for the proximally coated portion of tapered implant designs.
6. While traditionally, acetabular preparation and placement is performed prior to the femoral side, preparation limited to proximal and distal would be helpful in facilitating femoral retraction and preliminary gap measurements (between femoral cut and acetabular component).
7. It is the middle region reaming that determines and maintains the depth/height at which the final component resides.
8. Middle region reaming is the most destructive portion of reaming techniques and can be limited in:
    a. reamer cutting teeth length and
    b. number of reamer passes.
9. The number of middle reamer passes can be limited by
    a. accurately determining final implant size and depth,
    b. performing proximal and distal preparation separately and prior to middle region,
    c. performing middle region reaming after distal and proximal reaming.

The patent application is directed to devices and methods for hip replacement surgery. One aspect is directed to devices and methods for preparing the femoral canal for implanting a femoral component. This may include initially reaming a proximal region of the femoral canal and a distal region of the femoral canal. These regions are reamed without reaming a middle region of the femoral canal. The distal and proximal regions may be reamed in various orders (i.e., distal first or proximal first). In one embodiment, the femur is otherwise fully prepared in size and depth prior to the middle region reaming. At some time thereafter, the middle region is reamed. The middle region reamer level may be the final determinate of femoral component placement.

Another aspect is directed to the use of a dummy implant in the femoral canal. The dummy implant may include a portion that extends into the femoral canal and a section that extends outward. The dummy implant may be used for one or more of retraction of the femur, use with a measuring device to determine a gap with the acetabulum, and as a cutting block for making a revised femoral cut.

One embodiment disclosed is directed to a method of performing a hip replacement surgical procedure. The method includes: reaming distal and proximal regions of the femoral canal without reaming a middle region of the femoral canal with the middle region extending between the distal and proximal regions; inserting a dummy implant into the femoral canal; using the dummy implant for performing at least one of retracting the femur and determining a gap between an acetabulum and the dummy implant; after using the dummy implant, removing the dummy implant from the femoral canal and reaming the middle section of the femoral canal; and inserting a femoral component into the reamed femoral canal.

The method may include reaming the distal and proximal regions of the femoral canal with a single reaming tool having first and second cutting sections.

The method may include inserting the dummy implant into the femoral canal by positioning a plate at a proximal end of the dummy implant over a proximal end of the femur.

The method may further include inserting a mid-shaft reamer a single time into the femoral canal while reaming the middle region of the femoral canal.

The method may include that determining the gap between the acetabulum and the dummy implant includes attaching a tensometer to the dummy implant and gauging a distance to the acetabulum. The method may also include inserting a pivot pin of the tensometer into an opening in a plate of the dummy implant that extends outward beyond the femoral canal.

The method may also include positioning a soft tissue reamer protector at an end of the femur and inserting a mid-shaft reamer into the protector and reaming the middle region of the femoral canal. This may include contacting a stop flange on the mid-level reamer against the protector and limiting a depth of the reaming of the middle region of the femoral canal.

The method may include using a plate on the dummy implant that extends outward over the proximal end of the femur as a cutting guide and removing a portion of the proximal end of the femur.

The method may include using the dummy implant and retracting the femur and subsequently implanting an acetabular component.

The method may also include accessing the femur using an anterior trochanteric-based approach.

Another embodiment is directed to a method of performing a hip replacement surgical procedure. The method includes: preparing a distal region of the femoral canal without preparing a middle region of the femoral canal; preparing a proximal region of the femoral canal without preparing the middle region of the femoral canal; inserting a dummy implant with a first section extending within the proximal region, the middle region, and the distal region of the femoral canal, and a plate attached to the first section extending outward over a proximal end of the femur; attaching a tensometer to the plate and determining a gap between the femur and the acetabulum; cutting the proximal end of the femur along the plate; removing the dummy implant and preparing the middle region of the femoral canal without further preparing the distal region and the proximal region; and implanting a femoral component into the femur.

The method may further include contacting the dummy implant and retracting the femur away from the acetabulum and attaching an acetabular component to the acetabulum.

The method may include preparing the middle region of the femoral canal without further preparing the distal region comprises passing a mid-shaft reamer a single time along the middle region.

The method may include that the femoral component includes a unibody construction and accessing the femur with an anterior trochanteric-based approach.

The method may include preparing the distal region and the proximal region with a single tool that includes first and second cutting sections that are separated by a non-cutting section. The method may also include rotating the tool in a first direction and preparing the distal region with the first cutting section, and rotating the tool in an opposing second direction and preparing the proximal region with the second cutting section. The method may also include sliding the second section of the tool that includes the second cutting section over a first section that includes a first cutting section.

Another embodiment is directed to a method of performing a hip replacement surgical procedure. The method includes: reaming a distal region of the femoral canal with a distal reamer without reaming a middle region or a proximal region of the femoral canal; reaming the proximal region of the femoral canal with a proximal reamer without reaming the middle region or the distal region of the femoral canal; inserting a dummy implant into the femoral canal, the dummy implant including a first section that extends into the proximal region, the middle region, and the distal region of the femoral canal; positioning a plate on the dummy implant over a proximal end of the femur; applying a force to the dummy implant and retracting the femur; attaching a measuring tool to the plate of the dummy implant and measuring a gap between the femur and the acetabulum; cutting the proximal end of the femur along the plate; removing the dummy implant from the femur; after removing the dummy implant, reaming the middle region of the femoral canal without reaming the distal region or the proximal region; and implanting a femoral component and contacting the femoral component against the distal, proximal, and middle regions of the femoral canal.

The method may also include reaming the distal and proximal regions with a single tool that includes a distal cutting section and a proximal cutting section and an intermediation non-cutting section that aligns with the middle region when the tool is fully inserted into the femoral canal.

The method may include that the femoral component includes a unibody construction and accessing the femur with an anterior trochanteric-based approach.

These various aspects may be used together in a single procedure. Alternatively, the various aspects may be used separately to include just the use of the subsequent middle region reaming, and just the use of the dummy implant.

DETAILED DESCRIPTION

The present application is directed to methods and devices for performing hip replacement procedures. While this application could be directed to any hip replacement surgical procedure, it is most applicable for overcoming the difficulty of placing a long stem femoral component through anterior trochanteric-based approaches (i.e., Anterolateral, mini-Watson-Jones, Rottinger, Smith-Peterson, Matta modification).

The methods and devices include a reaming technique with initial proximal and distal reaming, followed by middle region reaming using a reamer with reduced cutting teeth length. The middle region reaming level is the final determinate of placement of a femoral component, and the femur is otherwise prepared in size and depth to receive the component before reaming with the middle region reamer. The middle region reamer includes reduced cutting teeth length and is passed definitively once to reduce and/or eliminate damage to nearby tissue. The technique further includes placement of a dummy implant within the femur. The dummy implant provides multiple functions, including but not limited to forming a cutting footprint for preparation of the femur, providing a cutting block for a revised femoral cut, providing a guide for sizing, providing a base for retraction of the femur, engagement with a tensometer, and for assisting with a lowering neck cut.

Figure 1:
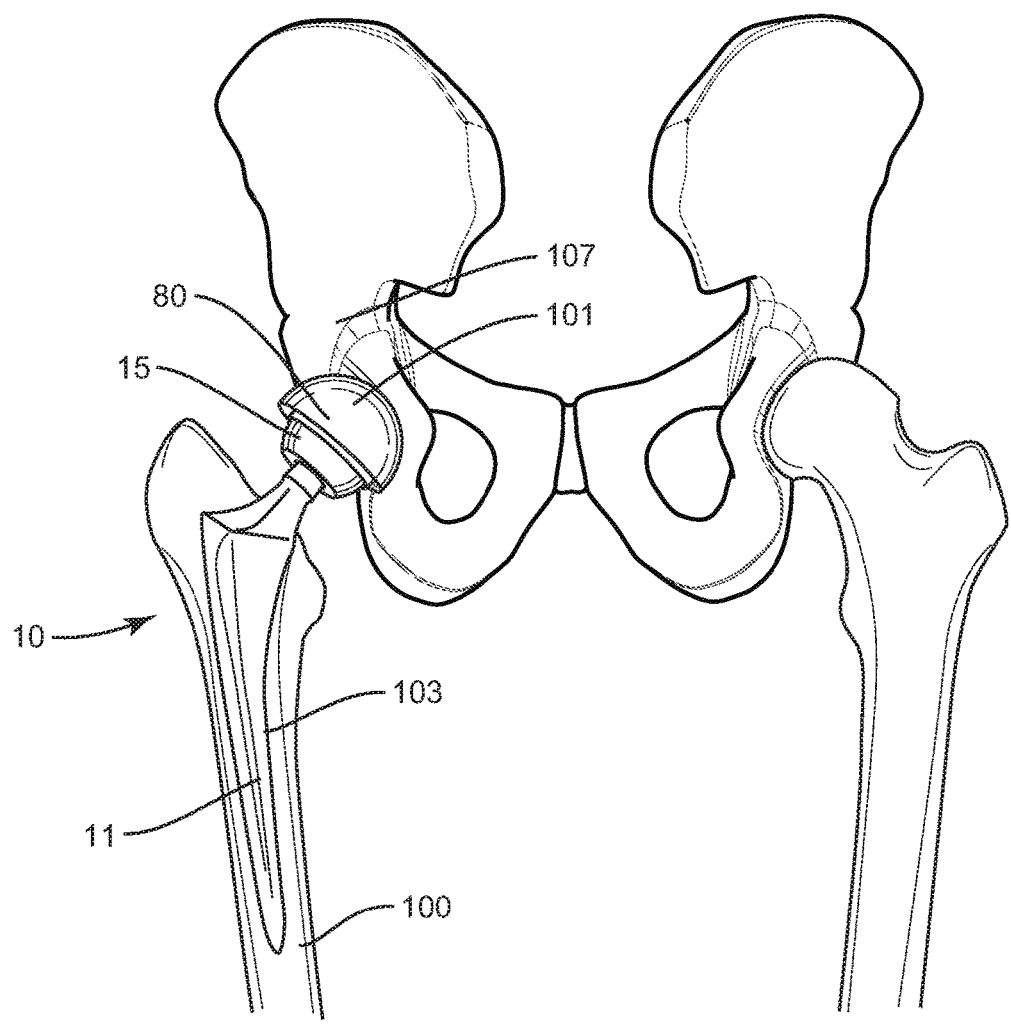
FIG. 1 is a side schematic view of a hip replacement implant mounted within a patient.

FIG. 1 illustrates a hip replacement implant 10 positioned within a patient. The implant 10 includes a femoral component 11 that is attached to the femur 100, and an acetabular component 80 that is attached to the acetabulum 101 in the pelvic bone 107. The femoral component 11 includes a head 15 that seats within a receptacle of the acetabular component 80. This replacement joint replicates the hip joint and provides for pivoting movement of the femur 100 relative to the pelvic bone 107.

Techniques disclosed in the present application include sizing of the femoral medullary canal 103 to receive the femoral component 11. This may include initial sizing of the femoral medullary canal 103 (hereinafter referred to as the femoral canal or canal 103) initially at distal and proximal locations. Sizing of a middle region of the canal 103 is subsequently performed and is the final determinate of the placement of the femoral component 11.

Figure 2:
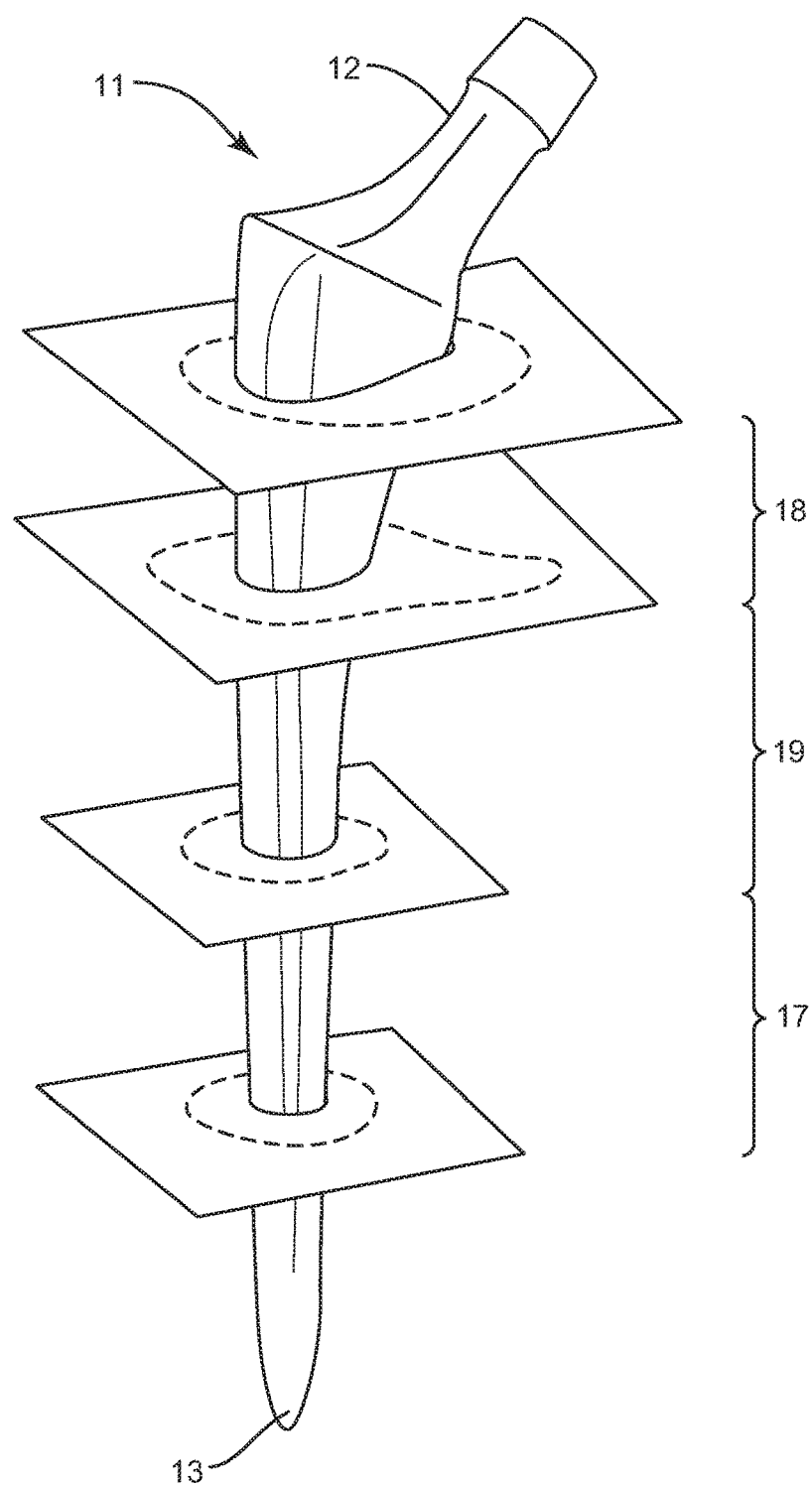
FIG. 2 is a perspective view of a femoral component with schematically indicated distal, proximal, and intermediate sections.

This concept is illustrated in FIG. 2 that includes the femoral component 11 with an elongated shape including a neck 12 and a distal tip 13. The distal region of the canal 103 is reamed to accommodate a distal section 17 of the component 11. Likewise, a proximal region of the canal 103 is reamed to accommodate a proximal section 18 of the component 11. After both the distal and proximal regions of the canal 103 have been prepared, a middle region is then reamed to accommodate a middle section 19 of the component 11.

Figure 3:
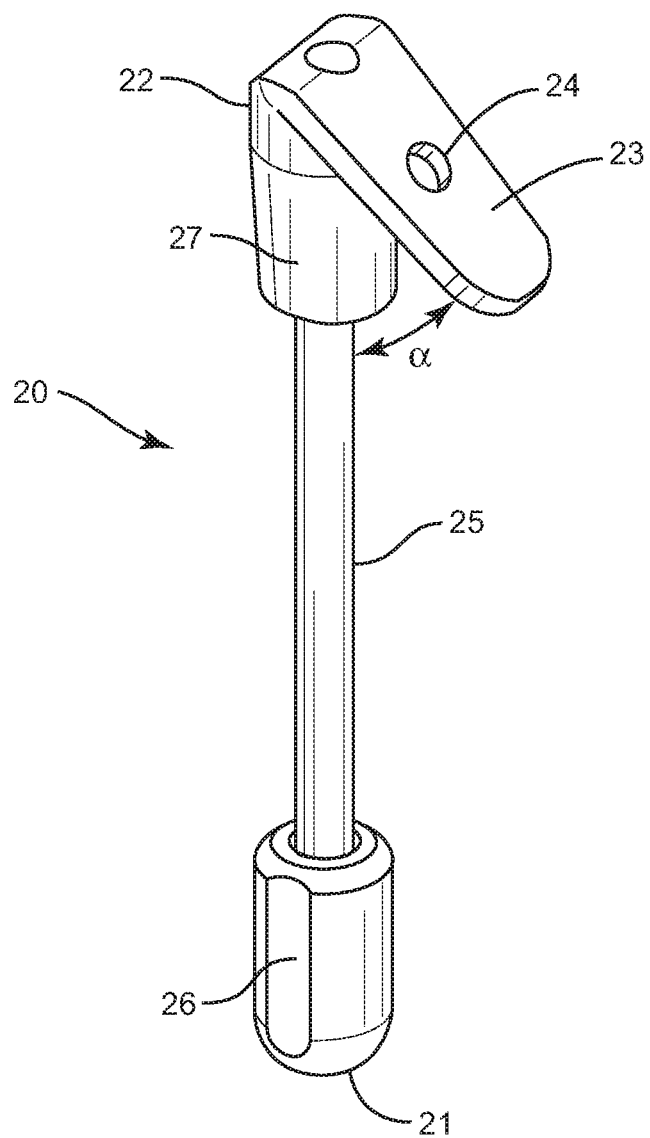
FIG. 3 is a perspective view of a dummy implant.

The extent of reaming of the distal and proximal regions of the canal 103 is determined using a dummy implant 20 that is inserted into the canal 103. The dummy implant 20 closely matches the cross-section of the distal section 17 and proximal section 18 of the femoral component 11. As illustrated in FIG. 3, the dummy implant 20 is sized to fit within the canal 103 after reaming of the distal and proximal regions. The dummy implant 20 includes a distal body 26 that corresponds to the size of the distal section 17 of the femoral component 11 and is sized to fit within the reamed distal region of the femoral canal. The dummy implant 20 also includes a shaft 25 with an enlarged section 27 that corresponds to the proximal section 18 of the femoral component 11 and is sized to fit within the reamed proximal region of the femoral canal 103. Because of the tapered shape of the femoral component 11, the enlarged section 27 includes a greater width than the distal body 26. In one embodiment, the tapered shape provides for a 3° taper between the enlarged section 27 and the distal body 26. A foot-plate 23 is positioned at the proximal end 22 and is sized and oriented to extend over the proximal end of the femur 100. The foot-plate 23 is positioned at an angle α relative to the enlarged section 27 to approximate the neck cut of the femur 100. An elongated shaft 25 extends between the enlarged section 27 and the distal body 26.

Figure 4:
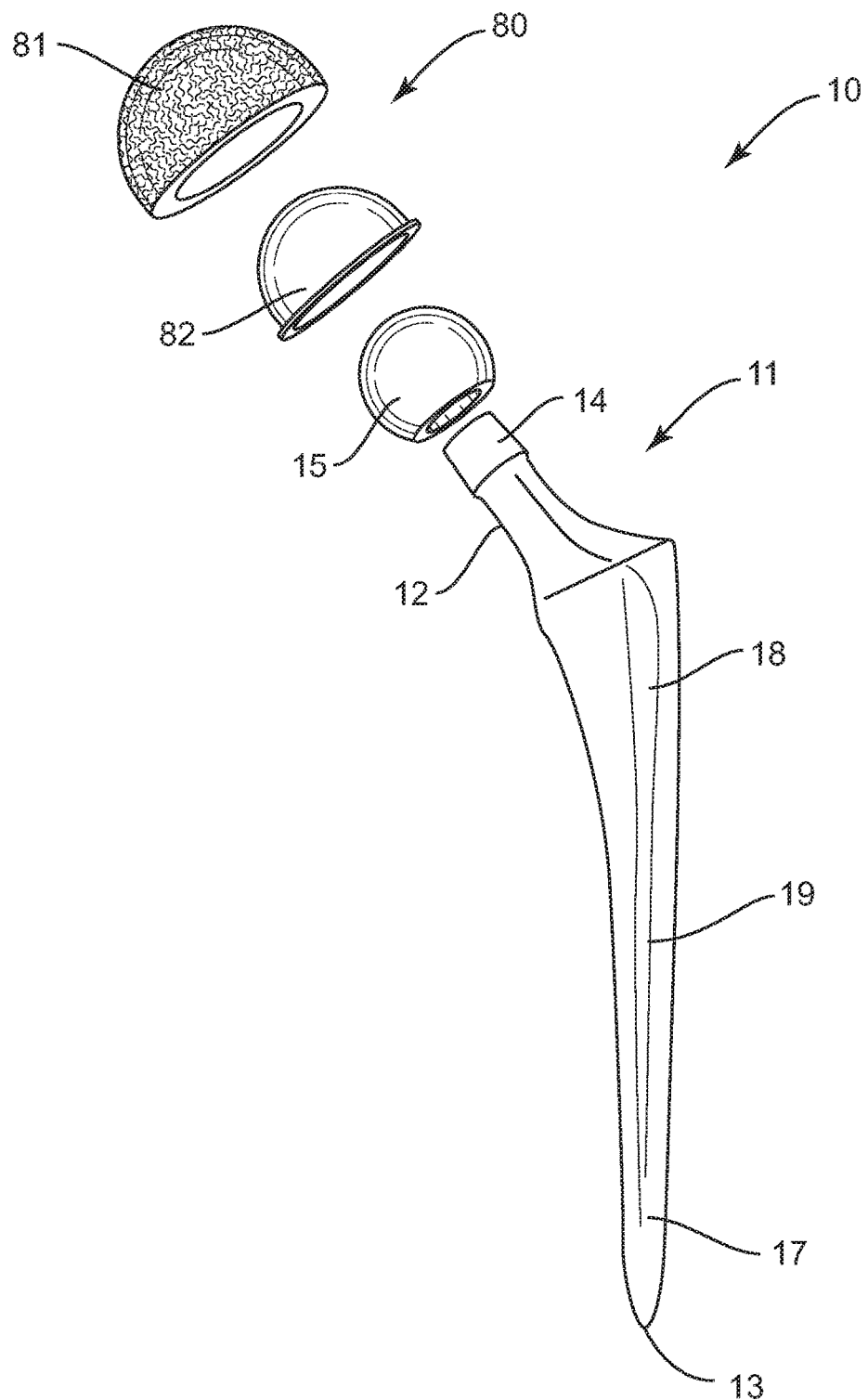
FIG. 4 is an exploded perspective view of a hip replacement implant including a femoral component and an acetabular component.

FIG. 4 illustrates one embodiment of an implant 10 that includes the femoral component 11 and the acetabular component 80. The femoral component 11 includes an elongated shape with a distal end 13 and the distal, proximal, and mid sections 17, 18, 19. The distal section 17 includes a generally circular cross-sectional shape, with the proximal section 18 having a substantially oval cross-sectional shape that increases in size in a proximal direction. The neck 12 extends laterally outward and includes a mount 14 to receive a head 15. The head 15 includes a receptacle that fits onto the mount 14 and a spherical exterior shape that engages with the acetabular component 80.

The acetabular component 80 is configured to attach to the acetabulum 101 and receive the head 15 of the femoral component 11. The acetabular component 80 includes a shell 81 and a liner 82 that each includes a concave shape. The shell 81 is initially attached to the acetabulum 101 with the liner 82 fitting within the shell 81. The liner 82 includes a receptacle sized to engage with the head 15 to form the joint.

Examples of implants 10 include but are not limited to a Synergy hip system with a Synergy Porous Plus HA femoral component available from Smith & Nephew of Memphis, Tenn., a Summit hip system available from Depuy J&J of Warsaw, Ind., and an Epoc Hip System available from Biomet of Warsaw, Ind.

Figure 5:
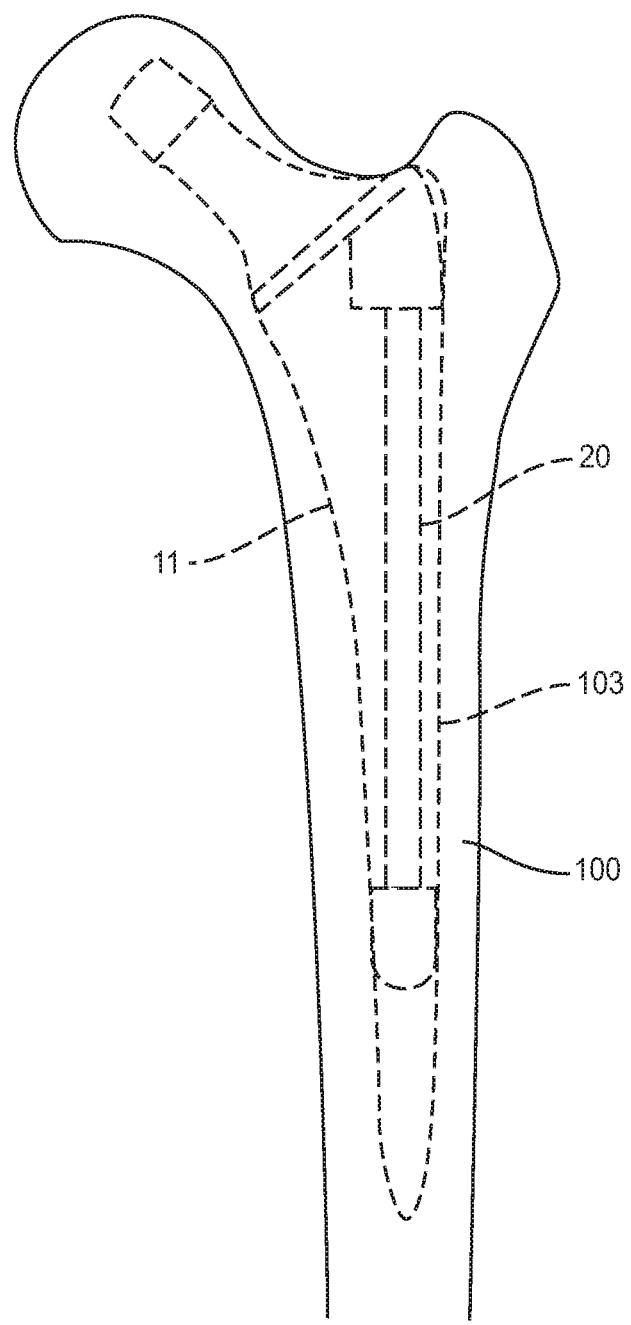
FIG. 5 is a side schematic view of the relative sizes, shapes, and positioning of a dummy implant and a femoral component relative to a femur.
Figure 5A:
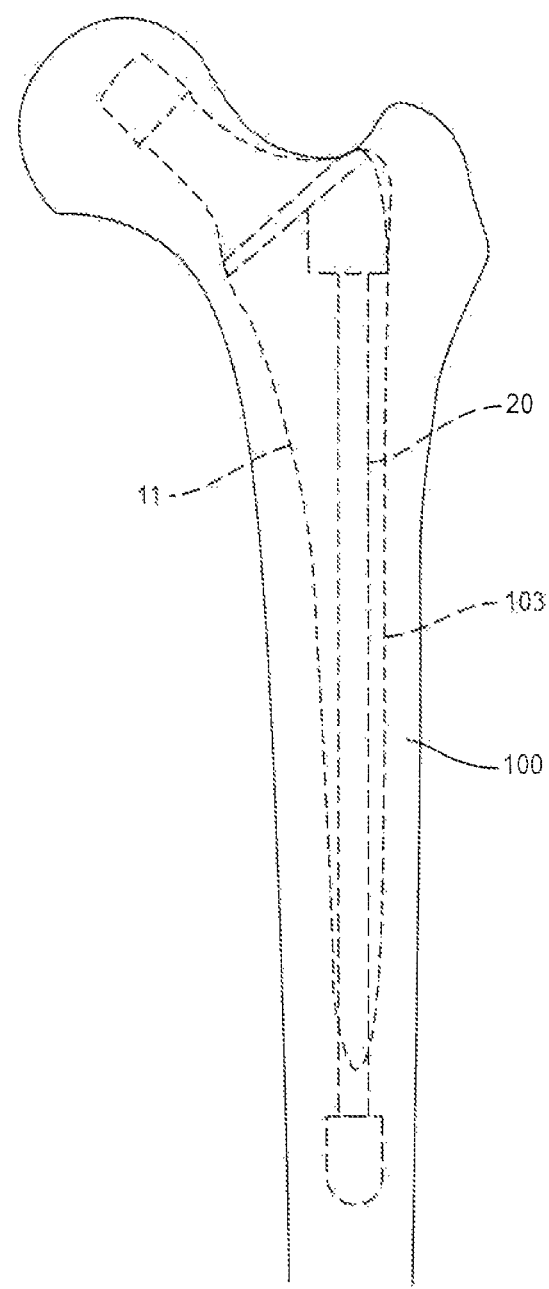
FIG. 5A is a side schematic view of the relative sizes, shapes, and positioning of a dummy implant and femoral component relative to a femur.

FIGS. 5 and 5A illustrate relative sizes, shapes, and placements of the dummy implant 20 and the femoral component 11 relative to the proximal femur 100. As illustrated, both the dummy implant 20 and femoral component 11 have shapes and sizes that correspond to the proximal femur 100. The femur 100 is initially prepared to receive the dummy implant 20. The dummy implant 20 is sized to fit within the femoral canal 103 and is configured to be used for a variety of different processes that are described in detail below. Once complete, the dummy implant 20 is removed and the femoral component 11 is implanted for forming a final component of the hip replacement implant.

Hip replacement procedures access the femur 100 and acetabulum 101 through various surgical approaches, including: approaches posterior to the trochanter such as the Southern, Moore, Gibson, Kocher-Langenbeck, maximum splitting, and posterolateral approaches. Other approaches include those anterior to the trochanter such as Smith-Peterson, Rottinger, Heuter, direct anterior, Watson Jones, lateral, anterolateral, abductor split, trans-gluteal, Bauer, trans-lateral, and Hardinge. Additional approaches may include trans-trochianteric approaches. The methods and devices of the present application are applicable to procedures using any of these approaches, or any approaches that may be favored by particular surgeons.

The described procedure uses an anterior approach. In general, an anterior approach is a more muscle sparing approach than a posterior approach. Hip replacement procedures using an anterior approach may result in a shorter recovery time for the patient because of the less invasive aspects of muscle-cutting requirements to access the surgical site. Further, anterior approaches may allow for the use of implants 10 that have historically resulted in a lower dislocation rate. In one embodiment, the methods and devices are used with the Rottinger procedure. The Rottinger procedure may be favored by surgeons for various reasons, including but not limited to: the procedure may be performed using a less-expensive operating table that places the patient in a lateral position; the ability to perform range of motion and stability testing after insertion of the implant 10; the ability to perform the procedure without the need for X-ray visioning; the reduction or elimination of issues with the femoral cutaneous nerve; and the wide applicability for use of the procedure with a variety of different femoral components 11.

Prior to the surgical procedure, preoperative planning may occur for determining an estimation of the range of component sizes. The planning includes the placement of templates of the prosthetic silhouette over radiographs of the hip. The templates have multiple sizes matching the multiple sizes of the available implants. The templates provide a reasonably accurate prediction of the final components size and placement. The templating is usually performed well in advance of the surgical procedure.

Once the preoperative planning is complete, the surgical phase of the procedure can commence. The patient is placed in a lateral position and secured on the bed in a stable position. A modified peg board is secured to the table to convert the table into a split configuration for the operative leg to be extended, abducted, and externally rotated for femoral preparation. The entire leg may be prepped and draped into the operative field for full range of motion and demonstration of hip stability once the trials and implants are implanted.

The actual placement of the surgical incision will depend on which surgical approach is being used. The general principles shared by all approaches include: an incision is made through the skin and subcutaneous tissue and fat, down to the fascia, which is usually incised in line with the skin incision. Once this first fascial layer is opened, the surgeon navigates past the muscles surrounding the hip, to expose the capsule of the hip joint. The capsule can be either opened for later closure or excised, but is usually preserved for later closure at the end of the procedure. Once the hip is exposed, either the femoral neck is osteotomoized, or the hip is dislocated and then the neck is osteotomized. If the osteotomy occurs first, then the femoral head will need to be removed at some point later in the procedure. Either way, once the femoral neck has been cut, the proximal femur is then exposed and mobilized.

The surgical site is established that provides access to the proximal section of the femur 100 and the acetabulum 101. While the hip can be dislocated with extension and external rotation, it is often safer to osteotomize the neck and remove the femoral head when the acetabulum 101 is fully exposed. Once the femur 100 is mobilized, a final cut is made on the femoral neck. Sometimes this osteotomy is performed in one cut, but often includes two cuts with the second cut attempting to make the level of the neck cut at approximately the final level. After the final femoral neck cut is made, the obturator externus tendon is detached from the femur 100. This allows for improved femoral exposure. With the neck and head of the femur 100 removed, the leg is brought back into a neutral position and the acetabulum 101 is exposed with placement of posterior and anterior acetabular retractors. The femoral head can be removed at this time.

The femur 100 is exposed with extension, adduction, and external rotation. In one embodiment, a two-pronged retractor is placed under the calcar medially to expose the cut surface of the proximal femoral neck. A box osteotome is used to open the femoral canal medial to the greater trochanter and centered in the femoral neck. Additional preparation, such as removing additional bone from the greater trochanter, may be necessary to form an adequate opening for receiving and positioning the femoral component 11.

Figure 6:
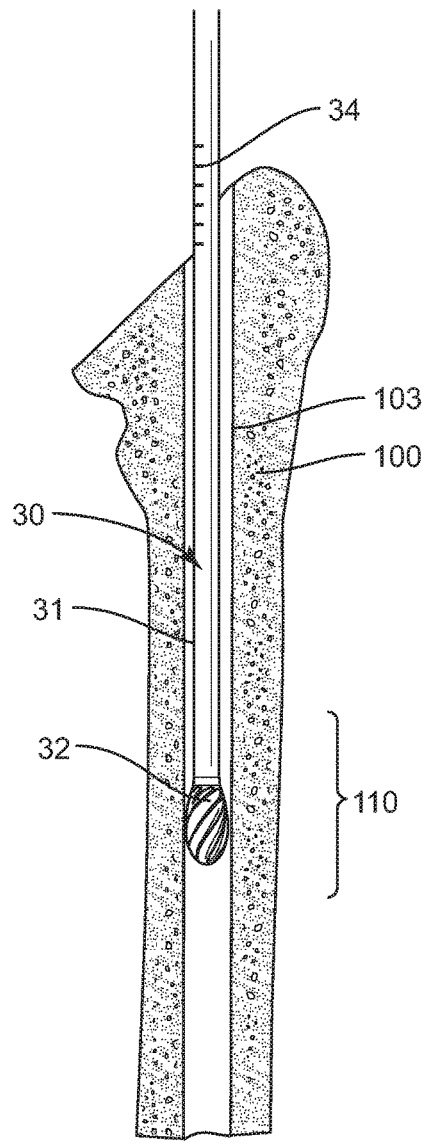
FIG. 6 is a side view of a distal reamer positioned in the femoral canal with the femur illustrated in cross section.

The femoral canal 103 is prepared by reaming the distal region 110 using a series of graduated distal reamers 30. FIG. 6 illustrates one of the distal reamers 30 for sizing the distal region 110 of the canal 103. The entire femoral canal is reamed with progressively increasing diameters until distinct resistance and chatter are obtained. The diameter of reamer, when this occurs will determine the femoral component size. This method of reaming not only determines implant size, but also reduces the chance of a pedestal being created by full length cutting reamers. Resistance seen with subsequent reamers, will unlikely be secondary to distal positioning or narrowing of the distal canal.

The distal reamer 30 includes an elongated shaft 31 with a ball head cutting section 32. The shaft 31 includes a relatively narrow width and is flexible to allow for the cutting section 32 to remain centered within the femoral canal 103. The shaft 31 may include a substantially smooth exterior surface and/or a circular cross-sectional shape to prevent damaging the tissue in proximity to the surgical site during rotation of the reamer 30. One or more markings 34 may be positioned along the shaft 31 that are visually aligned with the greater trochanter to determine a depth of the reaming. The cutting section 32 may include various configurations for sizing the femoral canal 103. The cutting section 32 may include a set of parallel straight or helical cutting edges. The edges may be orientated at an angle and include an underneath undercut. Helical edges may be aligned in either clockwise or counter-clockwise spirals.

Reaming of the distal region 110 is performed using a series of graduated reamers 30 with increasing diameter cutting sections 32. The reamers 30 are inserted into the femoral canal 103 in order with each subsequent reamer 30 being larger than the previous reamer. The initial reamer 30 may start at a diameter approximating 8 mm with subsequent reamers 30 increasing in size up to a diameter of 22 mm. The process may include insertion of graduated reamers 30 and reaming of the canal 103 to the point of chatter. At this point, the next reamer 30 in the series is passed along the distal section 110 for final reaming. The use of the one additional reamer 30 of greater diameter causes reaming around the entirety of the distal region 110 (i.e., 360 degree bone contact). This provides for engagement about the entire circumference of the distal section 17 when the femoral component 11 is finally implanted into the femur 100.

The size in diameter of the final distal reamer 30 determines the actual size of the implant 10. Implants 10 are often numbered from smallest to largest with either an arbitrary numbering system (e.g., 1-12) or a number system based on a diameter of the implant at a location/level on the actual implant such as the distal section. In one embodiment, a first implant has a distal diameter of 10 mm and a proximal diameter of 14 mm, with a second larger implant having an 11 mm distal diameter and a 15 mm proximal diameter. The location that defines the distal diameter for a given implant is somewhat arbitrary, but represents the intended level at which the component fully fills the canal 103. For the tapered stem design, this would be at the lower end of the distal section 17 as illustrated in FIG. 2.

The depth of insertion of the reamer 30 into the canal 103 may be determined by a visual mark 34 located along the shaft 31 that is aligned with the greater trochanter as determined during pre-operative planning. A surgeon may further rely on the tactile feel caused by contact of the reamer 30 within the interior wall of the canal 103 to determine the insertion depth. The surgeon should error on reaming further than the length of the eventual implant. There really isn't a depth limit to creating a symmetric canal at the final distal diameter. A continuous hollow cylinder does not leave a stress riser in bone or a pedestal to prevent implant subsidence. The depth markings 34 along the shaft 31 may be provided to ensure that the surgeon reams far enough to accommodate the implant.

Figure 7:
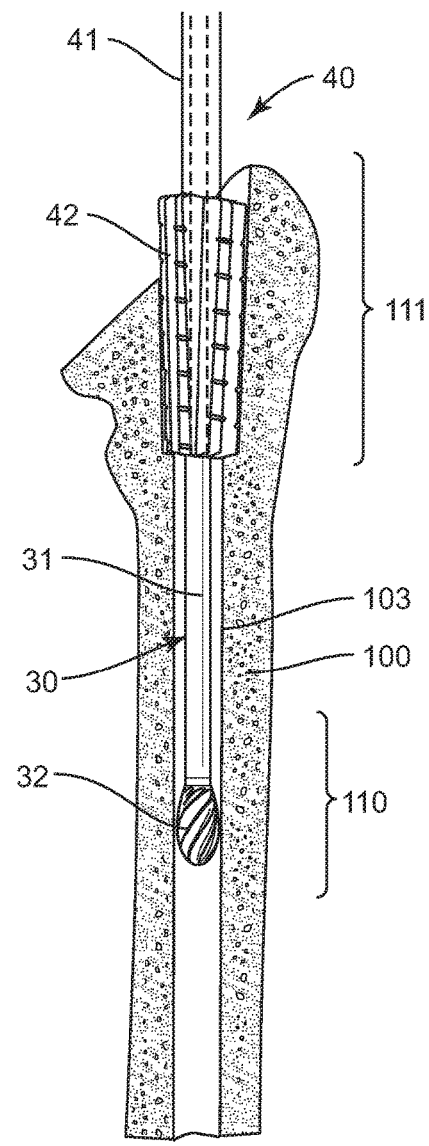
FIG. 7 is a side of a proximal reamer positioned over a distal reamer in the femoral canal with the femur illustrated in cross section.

After the distal reaming, a proximal reamer 40 is inserted to ream the proximal region 111 of the femoral canal 103. The proximal reaming shapes and sizes the canal 103 to accommodate the proximal section 18 of the femoral component 11. As illustrated in FIG. 7, the proximal reamer 40 may be configured to be used in conjunction with the distal reamer 30 by extending over the shaft 31 of the distal reamer 30 (the shaft 31 of the distal reamer that extends through the proximal reamer 40 is illustrated in dashed lines in FIG. 7). The proximal reamer 40 includes an elongated shape with a shaft 41 and a cutting section 42. A central opening extends longitudinally through both the shaft 41 and cutting section 42 to allow the proximal reamer 40 to be inserted over and moved along the shaft 31 of the distal reamer 30. The shaft 41 includes a circular cross-sectional shape with a smooth exterior surface to prevent damage to the nearby tissue during rotation of the reamer 40. The cutting section 42 may include the same or different cutting configuration as the cutting section 32 of the distal reamer 30. The cutting section 42 may include a set of parallel straight or helical cutting edges. The edges may be orientated at an angle and include an underneath undercut. Helical edges may be aligned in either clockwise or counter-clockwise spirals. In one embodiment, the cutting section 42 is oriented in an opposite direction from the cutting section 32 of the distal reamer 30. The proximal reamer 40 is rotated in an opposite direction than that of the distal reamer 30. This opposite orientation ensures that should the movement of the proximal reamer engage and move the distal reamer, that there is no reaming in the distal region 110 during the proximal reaming process.

The depth of insertion of the proximal reamer 40 into the canal 103 may be determined by a visual mark located along the shaft 41 that is aligned with the greater trochanter. Another manner of determining the insertion depth is the tactile feel caused by contact of the cutting section 42 with the interior wall of the canal 103. The depth of the proximal reaming is ideally enough to accommodate any revisions of the neck cut that may occur in subsequent steps of the surgical procedure.

During proximal reaming, the proximal reamer 40 is inserted over the shaft 31 of the distal reamer 30 and moved downward into the canal 103. The proximal reaming occurs during a single pass of a single proximal reamer 40 (i.e., there are no graduated reaming systems or multiple passes of the single proximal reamer 40). During the reaming, pressure may be applied to the proximal reamer 40 in the direction of the greater trochanter to lateralize the proximal region 111.

The cutting section 42 is positioned in the canal 103 prior to reaming to reduce and/or eliminate contact of the cutting section 42 with the surrounding tissue during rotation of the reamer 40. A portion of the cutting section 42 may extend outward from the canal 103 as illustrated in FIG. 7, but the amount that extends outward is limited and is usually contained within the retracted surgical site to prevent contact with the tissue. The first section 41 of the shaft that extends outward from the cutting section 42 is structured to prevent damage to the tissue in the event of contact. This structure may include a substantially smooth surface, and may also include a circular cross-sectional shape.

Each of the reamers 30, 40 are designed to prevent damage to the surrounding tissue. The proximal sections of the reamers 30, 40, particularly the shaft 31 of the distal reamer 30 and the shaft 41 of the proximal reamer 40, include surfaces designed to reduce and/or eliminate damage to the surrounding tissue in the event of contact. In one embodiment, the shafts 31, 41 are smooth and do not catch or otherwise cut or damage the tissue if there is inadvertent contact during the reaming of the canal 103. The cutting sections 32, 42 are positioned along the reamers 30, 40 to remain partially or completely positioned in the canal 103 during the reaming procedures.

One or both of the reamers 30, 40 may be operated by hand. Alternatively, one or both reamers 30, 40 may include a mount for attachment to a power tool for driving the reamers.

Figure 8:
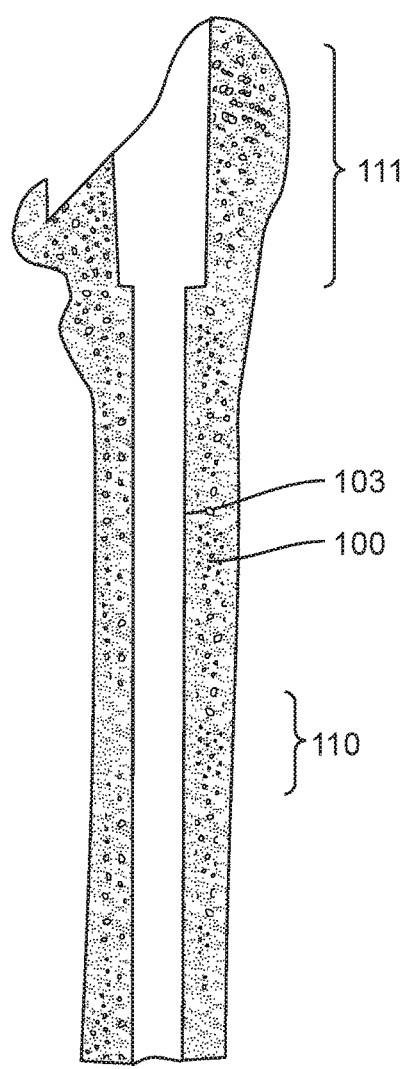
FIG. 8 is a cross-sectional side view of a femoral canal with reamed distal and proximal regions.
Figure 9:
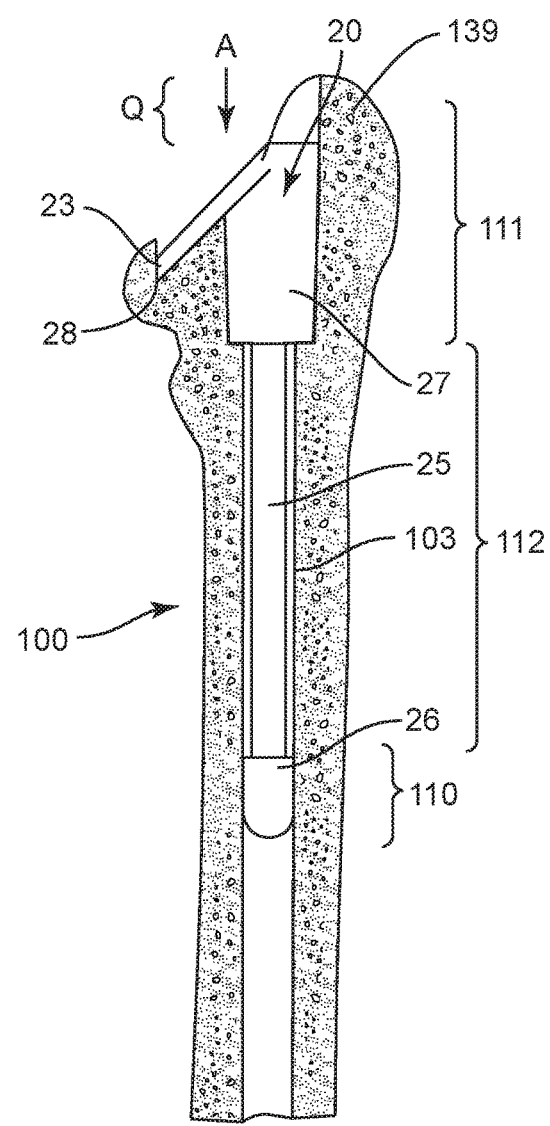
FIG. 9 is a side view of a dummy implant positioned in a femoral canal with the femur illustrated in cross section.

At this stage of the surgical procedure, the femoral canal 103 has been reamed along the distal and proximal regions 110, 111 as illustrated in FIG. 8. This sizing of the femoral canal 103 creates a silhouette that matches the shape and size of the dummy implant 20. FIG. 9 illustrates the dummy implant 20 inset within the femur 100. The dummy implant 20 seats in the femoral canal 103 with the distal body 26 aligned along the distal region 110 and the enlarged section 27 aligned along the proximal region 111. The distal body 26 contacts against the reamed distal region 110 of the femoral canal and the proximal section 27 contacts against the reamed proximal region 111 of the femoral canal. The elongated shaft extends between the enlarged section 27 and body 26 along the middle region 112 that is yet to be reamed. The shaft 27 is spaced away from this non-reamed middle region 112. Further, the foot-plate 23 extends over the top of the proximal femur and femoral neck. The dummy implant 20 substantially matches the dimensions of the femoral component 11 except for the section that aligns with the middle region 112 of the femoral canal 103.

The dummy implant 20 provides for numerous functions during the surgical procedure. The dummy implant may be used to perform one or more of the following functions: (1) shaping/cutting the proximal neck of the femur 100 to accommodate the femoral component 11; (2) providing a template for cutting a surface of the proximal neck of the femur 100; (3) sizing the femoral canal 103 relative to the femoral component 11; (4) retracting the femur; (5) engaging a tensometer to determine a neck length of the femoral component 11; and (6) potentially lowering the neck cut.

The first function includes cutting/crushing/compressing the cancellous bone within the proximal femoral neck during insertion of the dummy implant 20. The foot-plate 23 of the dummy implant 20 corresponds to the cross section of the final implant at that level. As illustrated in FIG. 9, the foot-plate 23 includes a cutting edge 28 along a lower surface. The cutting edge 28 may be isolated to just the tip of the foot-plate 23, or may extend along a larger section of the foot-plate 23. During insertion of the dummy implant 20 into the femoral canal 103 in the direction of arrow A, the cutting edge 28 contacts against a medial portion and cuts and shapes the femoral neck. The force necessary to cut the femoral neck may be applied by hand, or may require the use of a mallet that strikes against the upper surface of the foot-plate 23.

Figure 10:
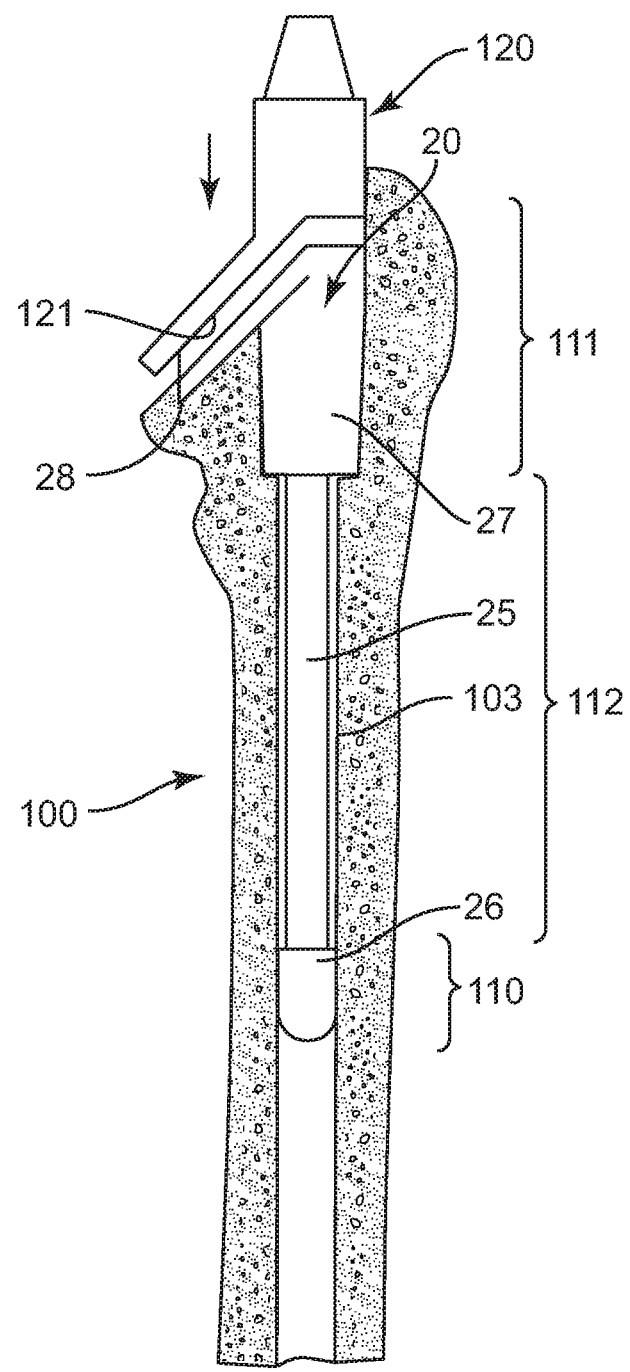
FIG. 10 is a side view of an impactor positioned relative to a dummy implant with the femur illustrated in cross section.

An impactor 120 may be used to apply a force to the dummy implant 20. As illustrated in FIG. 10, the impactor 120 includes a lower edge 121 that substantially matches the foot-plate 23 of the dummy implant 20. Force exerted on the impactor 120 is transferred to the dummy implant 20, and may be used to impact the dummy implant 20 by exact increments. The impactor 120 may be used if the surgeon wants to lower the neck cut on the femur 100.

Figure 11:
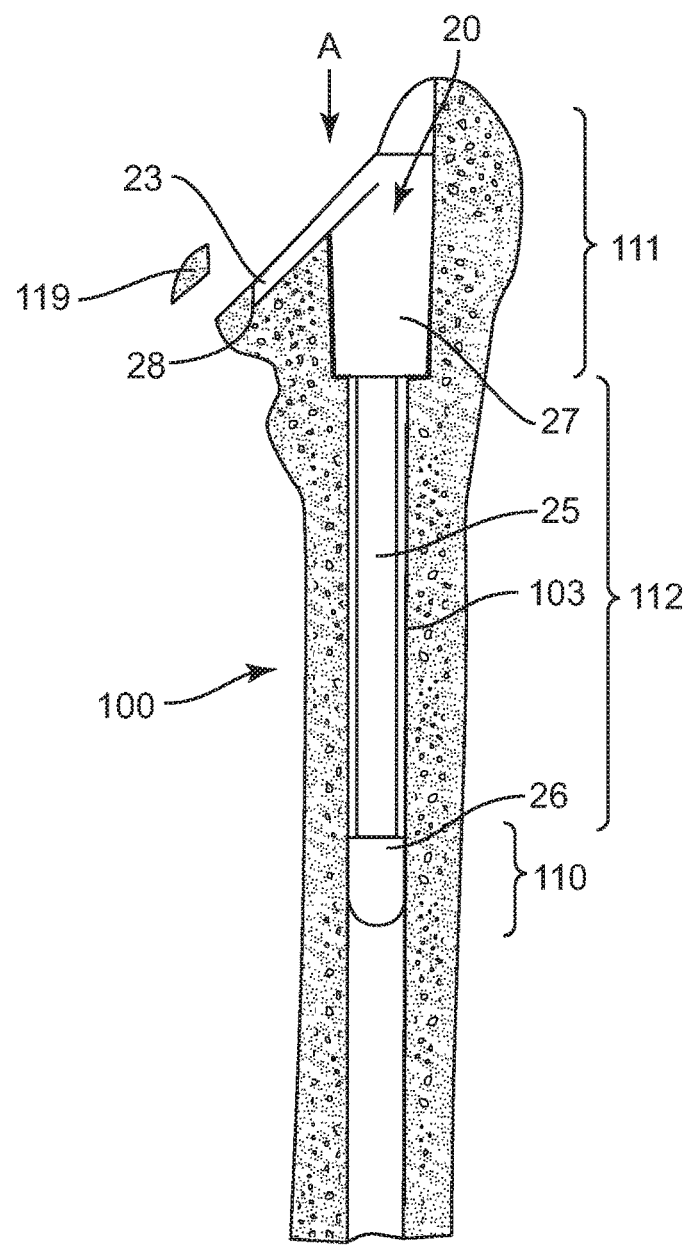
FIG. 11 is a side view of a dummy implant used as a cutting guide with the femur illustrated in cross section.

The second function of the dummy implant 20 is to provide a cutting template for the final femoral neck cut. Prior to this point, a rough estimate of the neck cut has been made during the surgical procedure. The dummy implant 20 seats within the femoral canal 103 with the foot-plate 23 positioned within an interior portion of the proximal end of the femur 100. The exposed proximal end of the femur 100 may include an uneven shape with one or more portions 119 extending above the top surface of the foot-plate 23. As illustrated in FIG. 11, the upper surface of the foot-plate 23 functions as a cutting guide to remove the one or more portions 119. The upper surface is substantially flat and forms an alignment surface against which the surgeon may position a blade of a cutting instrument. The blade is moved along the length of the foot-plate 23 thereby removing the one or more portions 119 that extend superiorly beyond the foot-plate 23.

Figure 12:
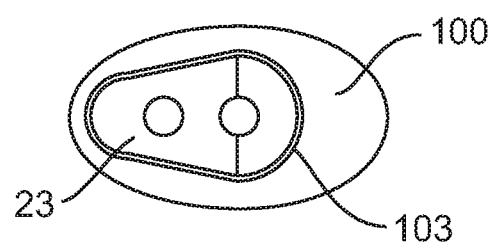
FIG. 12 is a top view of a dummy implant positioned in a femoral canal.

The third function includes sizing the femur 100 relative to the dummy implant 20. The foot-plate 23 of the dummy implant 20 matches the dimensions of the proximal section 18 of the femoral component 11. Further, the dimensions of the distal body 26 match distal section 17 of the femoral component 11. This matching provides an indication to the surgeon about the fit and placement within the femoral canal 103. The dummy implant 20 also provides the first visual indication of how the implant will seat within the femur 100. As illustrated in FIG. 12, the foot-plate 23 replicates the shape of the proximal section 18 of the femoral component 11 (see FIG. 2) allowing the surgeon to visually determine the position relative to the femoral canal 103 and femur 100. Based on the tactile feel of the dummy implant 20 within the femoral canal 103 and/or the visual placement of the dummy implant 20 relative to the femur 100, the surgeon is able to determine if adjustments are necessary.

As illustrated in FIG. 9, the dummy implant 20 is inserted into the femoral canal 103 with the distal body 26 contacting against the wall of the femoral canal 103 and the shaft 25 being spaced away from the wall of the femoral canal 103. The footplate 23 at the proximal end of the dummy implant 20 is contacted against the proximal end of the femur 100. The dummy implant 20 is sized and shaped to be inserted into the femoral canal 103 such that the footplate 23 is positioned below the superior end of the greater trochanter 139 by a distance Q. Once the dummy implant 20 is located at this position in the femoral canal 103, the expected position of the femoral component 11 relative to the femur 100 can be determined by visually observing the position of the dummy implant 20.

Figure 13:
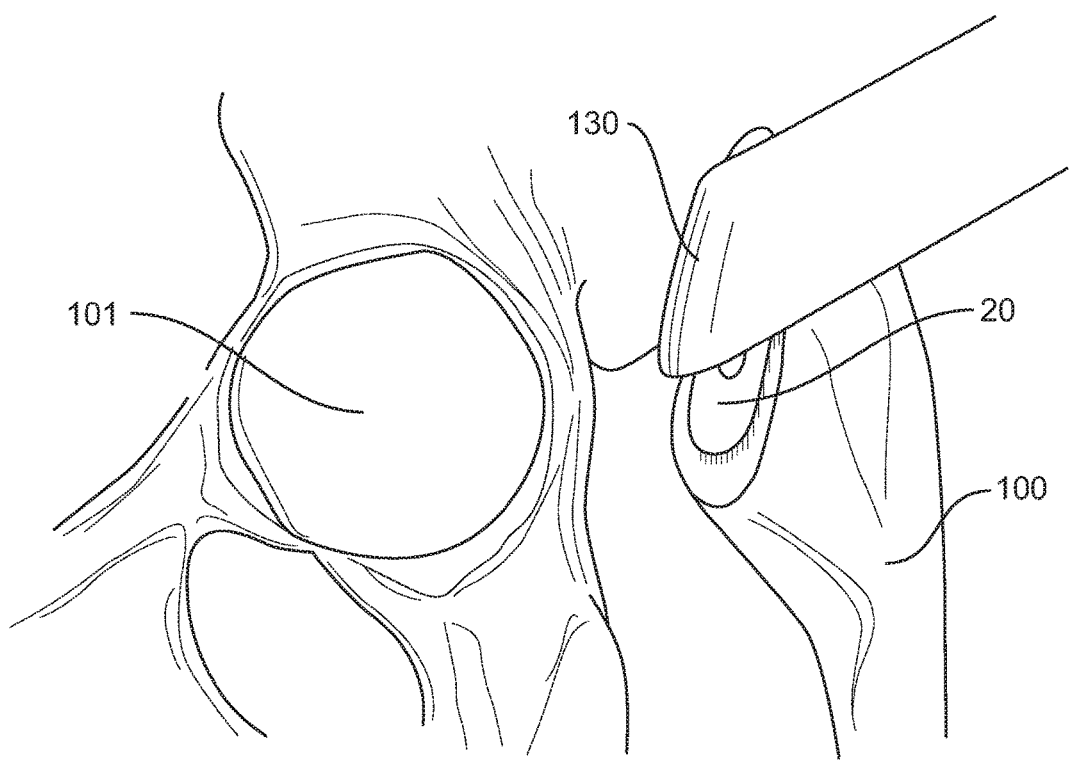
FIG. 13 is a perspective view of a retractor engaged with a dummy implant.

The fourth function of the dummy implant 20 is to retract the femur 100 away from the acetabulum 101. The dummy implant 20 that extends outward from the femur 100 provides an attachment that can link to a cobra retractor and be used to retract the femur 100. FIG. 13 illustrates a retractor 130 engaged with the dummy implant 20 to retract the femur 100 away from the acetabulum 101. The dummy implant 20 protects the integrity of the proximal femur 100 and the femoral neck while the cobra retractor 130 forcibly pushes the femur 100 aside for acetabular preparation. Previous retraction methods have included applying a force directly to the femur 100 at a location at or in proximity to the proximal femur 100.

Once the femur 100 is being retracted through the dummy implant 20 as illustrated in FIG. 13, the acetabulum 101 is then reamed to form an area for receiving the acetabular component shell 80. Once the acetabulum 101 is prepared, the acetabular component 80 is placed within the patient and attached to the acetabulum 101 using various methods, including one or more bone screws. Bone screws may be used to attach the shell 81 to the acetabulum 101, with the liner 82 being subsequently placed over the bone screws and attached to the shell 81. The liner 82 is positioned to later receive the head 15 of the femoral component 11.

Figure 14:
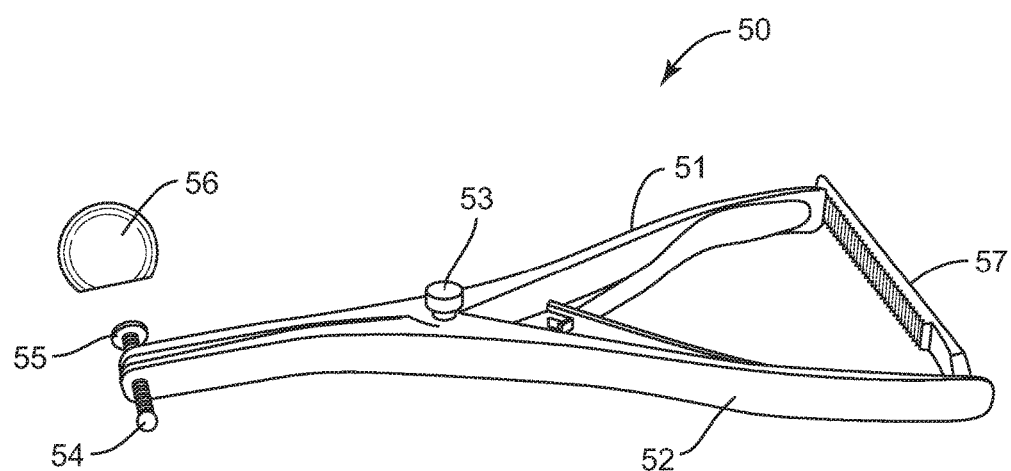
FIG. 14 is a perspective view of a tensometer.

The fifth function of the dummy implant 20 is for use with a tensometer 50 to determine a distance between the femoral neck cut and the acetabular hip center. This gap between the acetabular component 80 and the implant 20 determines the neck size for the femoral component 11. Preferably, components 11, 80 can be positioned to minimize of eliminate the neck. FIG. 14 illustrates a tensometer 50 to measure the gap. The tensometer 50 includes a pin 54 at the first end of the handle 52 sized to fit in the opening 24 in the foot-plate 23 of the dummy implant 20. The end of the pin 54 may include a spherical shape to engage with the opening 24. Once the pin 54 is attached to the dummy implant 20, a spherical head 56 at the first end of the handle 51 is seated into the acetabulum component 80. The distance between the components is measured to determine the necessary neck length on the femoral component 11. Ideally, tactile and/or audible feedback occurs when the spherical head 56 seats into the acetabulum component 80 to indicate solid engagement.

Figure 15:
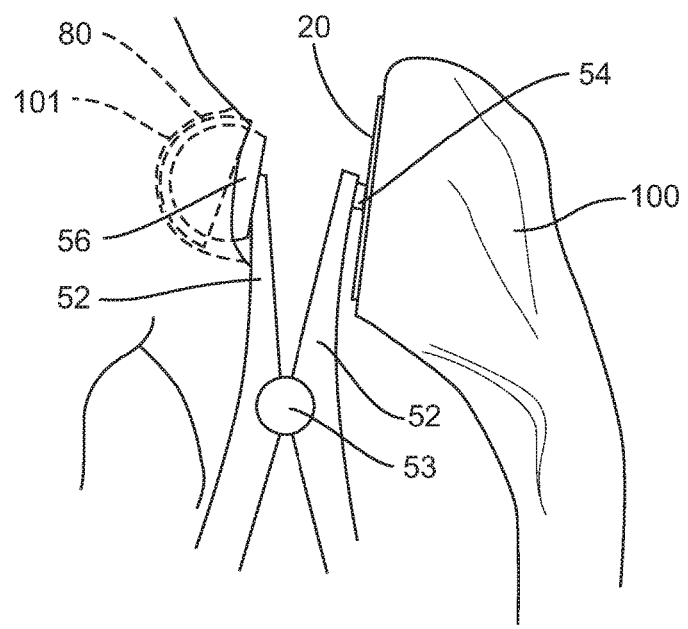
FIG. 15 is a side view of a tensometer positioned to measure a gap between a femur and acetabulum.

FIG. 15 illustrates an embodiment of the tensometer 50 positioned to determine a distance between the acetabular hip center and the femoral neck cut. The spherical head 56 is seated in the acetabulum component 80 on the acetabulum 101, and the pin 54 is mounted to the dummy implant 20.

Figure 16:
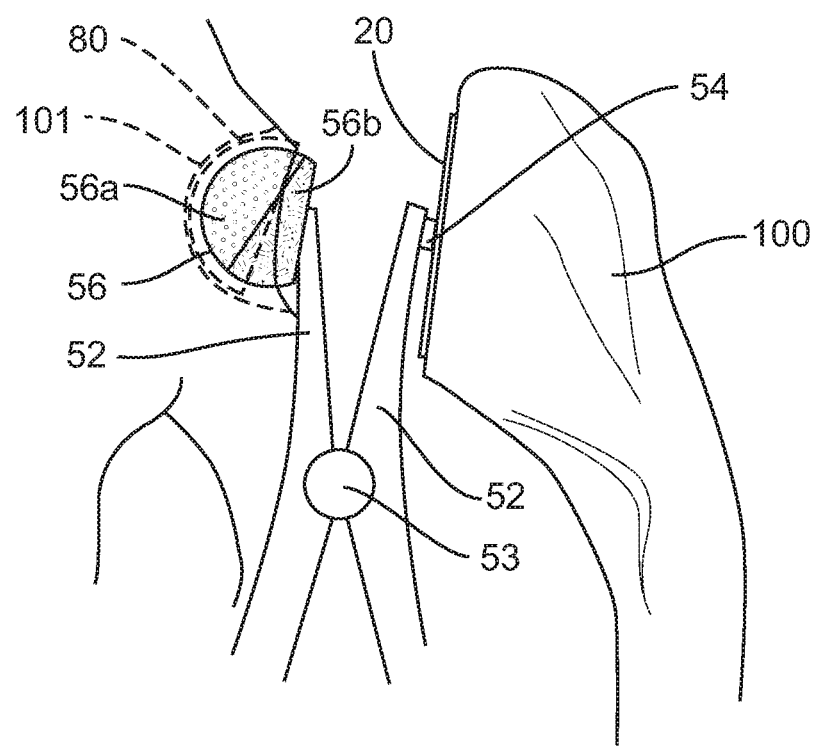
FIG. 16 is a perspective view of a tensometer with the head including two visually distinct sections.

While the femoral component 11 is defined by the proximal anatomy of the femur 100, the acetabulum component 80 can be orientated/rotated freely in all directions. If the component 80 is not oriented properly to the femur 100, hip instability could occur. The combined version (sum of the cup and stem anteversion) has been reported to be in the 25-45 degree range. To address this issue, the tensometer 50 will have a dual purpose. In addition to assessing space/tension between the femur and acetabulum (head/neck length), it will also be able to assess cup version in relationship to the acetabulum. The head 56 of the tensometer 50 will have incorporated the ideal version/relationship sought by the surgeon, by dividing the femoral head 56 into two sections 56a, 56b as illustrated in FIG. 16. The two sections 56a, 56b are visually differentiated, such as through the use of two different colors. When the circumference of the acetabulum component 80 overlaps the line between the two sections 56a, 56b, proper cup version has been obtained. If portions of the two sections 56a, 56b can be simultaneously seen by the surgeon, when the ball is reduced and with the leg in a neutral position, then the version is outside parameters and the surgeon should re-orientate the acetabular component 80, prior to proceeding on to the femoral component 11.

The sixth function of the dummy implant 20 is to provide a gauge for determining how to further treat the femur 100. If the engagement between the spherical head 56 and the acetabulum component 80 is correct, then no further treating of the femur 100 is necessary and the dummy implant 20 can be removed from the femur 100. If the measured gap is too long indicated by the engagement of the spherical head 56 and acetabulum component 80 being too tight, the dummy implant 20 can be impacted a set distance further into the femur 100 and re-cut (see FIG. 10). The additional cut lowers the position of the dummy implant 20 relative to the femur 100. Once the revision cut is complete, another gap measurement may be taken to determine whether the gap is now adequate. If the measured gap is too short with an engagement that is too loose, the depth of reaming of the middle region 112 of the femoral canal 103 will be adjusted to accommodate for the shortness as will be described below.

Figure 17:
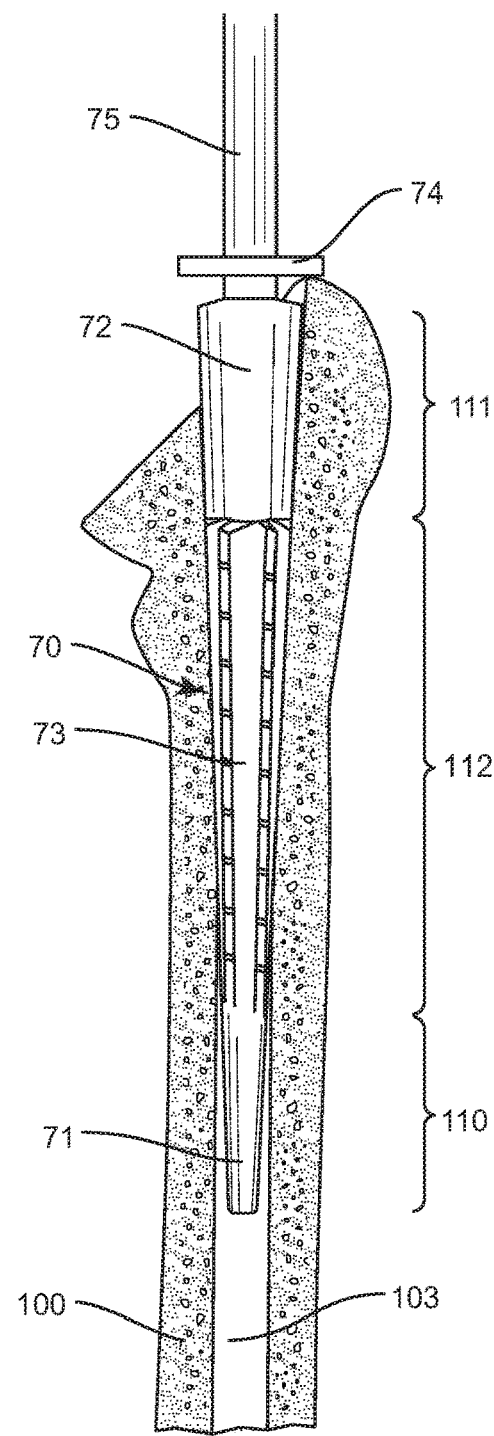
FIG. 17 is a side view of a mid-shaft reamer positioned in the femoral canal with the femur illustrated in cross section.

Once the various procedures with the dummy implant 20 are complete, the implant 20 is removed from the femur 100. Once removed, reaming of the middle region 112 of the femoral canal 103 is performed using a mid-shaft reamer 70. This final mid-shaft reamer 70 matches the diameter of the implant size determined during the distal reaming. As illustrated in FIG. 17, a mid-shaft reamer 70 is inserted into the canal 103 for reaming the middle region 112 positioned between the distal and proximal regions 110, 111 and that has not previously been prepared by the distal or proximal reamers 30, 40. The mid-shaft reamer 70 includes an elongated shape with a distal section 71 that aligns with the previously-reamed distal region 110, and a proximal section 72 that aligns with the previously-reamed proximal region 111. Each of these previously-reamed sections 71, 72 match the shape of the femoral component 11 and function to center the mid-shaft reamer 70 along the femoral canal 103.

The sections 71, 72 each include a smooth exterior surface such that there is no additional reaming of the distal and proximal regions 110, 111. A cutting section 73 is positioned along an intermediate length of the reamer 70 between sections 71, 72. The cutting section 73 includes a tapered shape with cutting surfaces similar to the cutting sections 32, 43 of the reamers 30, 40 as described above. The diameter of the cutting section 73 is paired but not identical to the last diameter of the distal reamer 30. The diameter of the cutting section 73 also matches the proximal diameter of the femoral implant 11. A shaft 75 extends outward in a proximal direction from the second section 72. The shaft 75 may include a smooth exterior surface and a circular cross-sectional shape to prevent damage in the event of contact with the tissue.

The depth of reaming of the middle region 112 may be controlled in various manners. A flange 74 is positioned along the shaft 75 and includes a greater width than the shaft 75. The flange 74 functions as a depth stop and contacts against or otherwise be aligned with the femur 100 to control an extent of reaming of the femoral canal 103. The flange 74 may be adjustable along the length of the shaft 75 to accommodate variations in the desired reaming levels. The level of the flange 74 is determined in part by the measurements taken from the tensometer 50. The flange 74 is adjustable in height/position and may be adjusted along the shaft to accommodate the implant when the gap measured between the dummy implant 20 and the acetabular component 80 is too loose. The insertion depth of the mid-shaft reamer 70 may also be controlled by the size of the distal section 71. The size of the distal section 71 causes engagement with the reamed distal region 110 and prevents further insertion into the femoral canal 103.

Preferably, the previous preparation (proximally, distally, and footplate) allows the surgeon to perform a single pass with one mid-shaft reamer 70 to size the middle region 112 (as opposed to multiple passes using a graduated, multiple reamer system such as that disclosed for reaming the distal region 110). This single pass includes moving the mid-shaft reamer 70 along the middle region 112 in a first direction into the canal 103, and then moving the reamer in an opposing second direction out of the canal 103. This single pass reduces the potential for damage to the nearby tissue and over-reaming of the canal 103.

Figure 18:
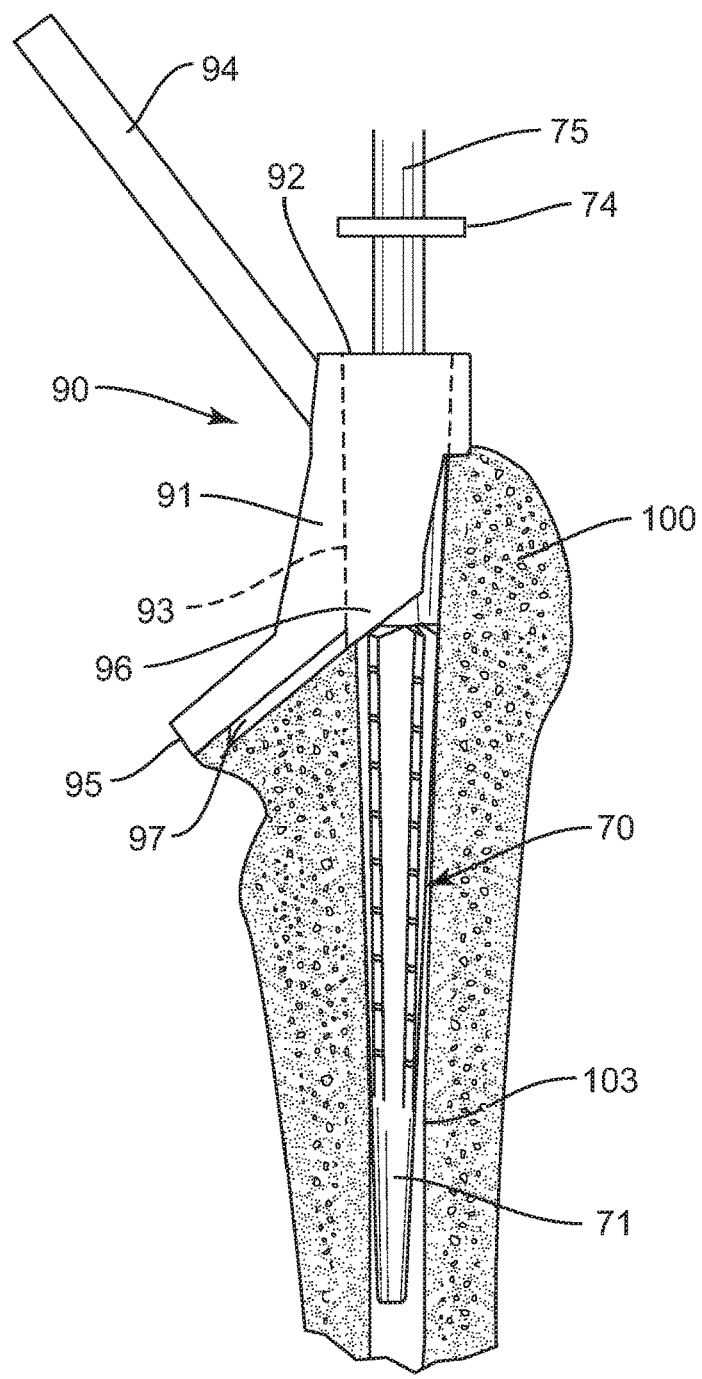
FIG. 18 is a side view of a protector positioned at a proximal end of the femur and with a mid-shaft a reamer positioned in the femoral canal with the femur illustrated in cross section.

As illustrated in FIG. 18, the mid-shaft reamer 70 may be used with a soft-tissue reamer protector 90 to protect the femur 100 and control a depth of reaming of the canal 103. The protector 90 includes a body 91 that is shaped to match the diameter of the proximal reamer 40. The body 91 includes a channel 93 to allow for passage of the mid-shaft reamer 70. A contact surface 92 is positioned on an outer side of the body 91 in proximity to the channel 93. An arm 94 may extend outward from the body 91 to allow for the placement and manipulation of the protector 90 by the surgeon. The protector 90 also includes an angled flange 95 with an inferior surface 96 that is at the same angle as the foot-plate 23 of the dummy implant 20 and matches the dimensions of the uppermost area of ingrowth on the final implant. The flange 95 sets on top of the femoral neck cut and is not inset into the same area 97 where the dummy implant 20 resided (i.e., the flange 95 sets on top of the cut edge with the recessed area 97 left by the dummy implant 20 being empty). In another embodiment, the protector 90 includes an adjustable lip underneath the flange 95. The lip is inset into the recessed area where the dummy implant 20 resided.

In use, the protector 90 is placed at the proximal end of the femur 100 with the channel 93 being aligned with the femoral canal 103. The surgeon than inserts the reamer 70 through the channel 93 and into the canal 103 to ream the middle region 112. The body 91 protects the proximal end of the femur 100 from being directly contacted by the reamer 70 or a device driving the reamer 70 either of which could potentially damage the femur 100. Further, the first section 71 of the reamer 70 may be equipped with a stop flange 74 that is wider than the channel 93 and contacts against the surface 92 to prevent further insertion and hence the reaming depth along the canal 103. The stop flange 74 may be adjustable along the longitudinal length of the reamer 70 to set the reaming depth. Further, indicia may be displayed along the length to indicate the placement of the stop flange 74 and the resulting reaming depth. Once reaming is complete, the reamer 70 and the protector 90 are removed from the patient.

Figure 19:
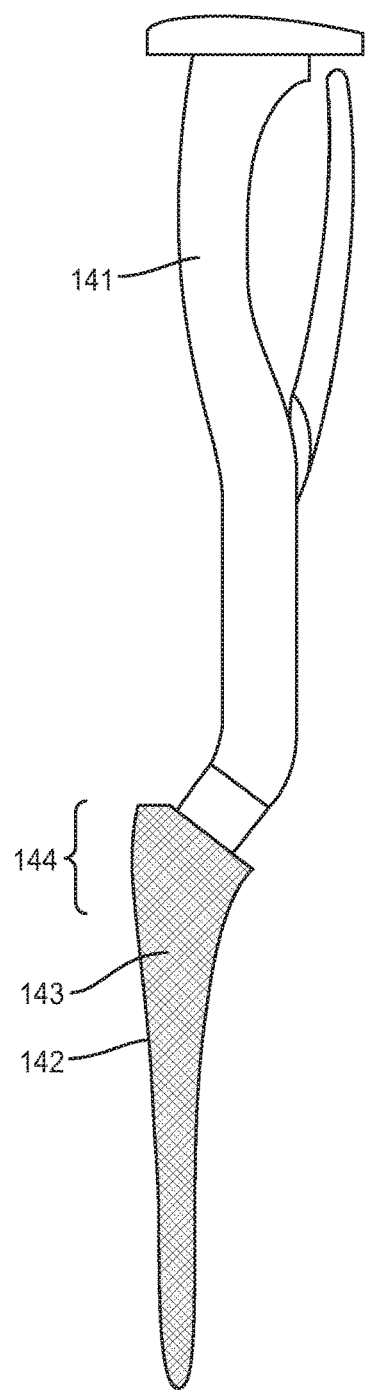
FIG. 19 is a side view of a rasp.

Additional sizing of the canal 103 may occur prior to insertion of the femoral component 11. This may include the insertion of one or more rasps 140 to further enlarge the size of the canal 103 as appropriate to receive the femoral component 11. The size of the rasp matches the dimensions from the implant size determined during the distal reaming. FIG. 19 illustrates a rasp 140 that includes a handle 141 with a cutting section 142 with teeth 143 positioned along the outer surfaces.

The rasp has three potential functions: 1) to connect together the previous areas of preparation; 2) to remove cancellous bone inside the canal within the flair of the femoral canal location medial the area previously machined by the reamers; and 3) to be potentially used as a trial component for range of motion (after a neck and head are placed on the rasp, it can be reduced into the acetabulum and put through a range of motion). The concept of the rasp is not new. Most companies producing implants currently have these rasps available in sizes matching all of the available femoral components. The rasp may treat one or more portions of the femoral canal 103 and form transitions between the distal, proximal, and middle regions 110, 111, 112. The rasp 140 connects the three separate regions that were separately reamed during the process.

Once the canal 103 is finalized, the femoral component 11 is inserted into the canal 103. One or more trial reductions are performed to assess the engagement of the femoral and acetabular components 11, 12. The joint formed by the head 15 placed within the receptacle of the acetabular component 11 is analyzed to determine adequate joint stability, range or motion, and restoration of leg length and offset. Final adjustments to the implant may be made accordingly. Once complete, the procedure is finalized by closing the surgical site.

The procedures described above include the three-section reaming process in combination with the use of a dummy implant 20. These different procedures may also be performed independently of one another. By way of example, a procedure may include a three-section reaming process without the use of a dummy implant 20. Similarly, a dummy implant 20 may be used without sizing the canal 103 with the three-section reaming process.

The distal, proximal, and middle regions 110, 111, 112 of the canal 103 and the corresponding sections 17, 19, 18 of the femoral component 11 may have different lengths measured along the axis of the canal 103. The lengths disclosed in FIG. 2 are one embodiment, with other embodiments including different lengths in one or more of the sections 17, 18, 19. In one embodiment, the length of the middle region 112 is greater than either of the distal and proximal regions 110, 111.

FIG. 2 illustrates one embodiment of a hip replacement implant 10. Various other implants 10 may also be used with the methods and devices disclosed in the present application.

The reaming on the canal 103 may initially include reaming of the distal region 110 followed by reaming of the proximal region 111 as illustrated and described above with reference to FIGS. 6 and 7. Alternatively, the proximal region 111 may be initially reamed followed by the distal region 110.

In a preferred embodiment, the middle region 112 of the canal 103 is reamed definitively once during the procedure. This reduces the potential for damage to the nearby tissue and over-reaming of the canal 103. Other embodiments may include making repeated passes with the reamer 70 through the middle region 112.

The protector 90 may be used with the mid-shaft reamer 70 as illustrated in FIG. 18. The protector 90 may further be used with the distal reamer 30 and/or the proximal reamer 40. The reamers 30, 40 may be equipped with flanges to be used with the protector 90 to control the reaming depth.

The proximal reamer 40 may include a variety of different configurations. In one embodiment, the proximal reamer 40 is cannulated and extends over the shaft 31 of the distal reamer 30. In use, the proximal reamer 40 is inserted over the shaft 31 of the distal reamer 30 while the distal reamer 30 remains in the femoral canal 103. In this embodiment, the cutting section 42 of the proximal reamer 40 is oriented in an opposing direction than the cutting section 32 of the distal reamer 30. This opposite orientation provides for just the proximal reamer 40 to be reaming the femoral canal 103, with any rotation imparted to the distal reamer 30 resulting in no material being removed from the femoral canal 103. In another embodiment, the distal reamer 30 is removed from the femoral canal 103 prior to attaching the proximal reamer 40. The proximal reamer 40 is positioned at the appropriate location along the length of the shaft 31 of the distal reamer 30 and locked into position. The attached distal and proximal reamers 30, 40 are then together placed into the femoral canal 103.

Figure 20:
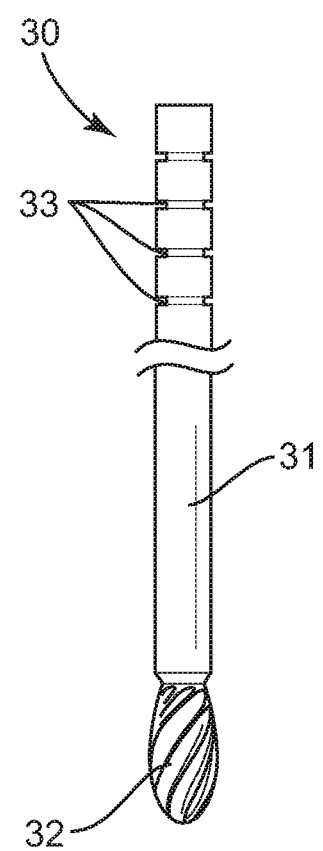
FIG. 20 is a side view of a distal reamer.
Figure 21:
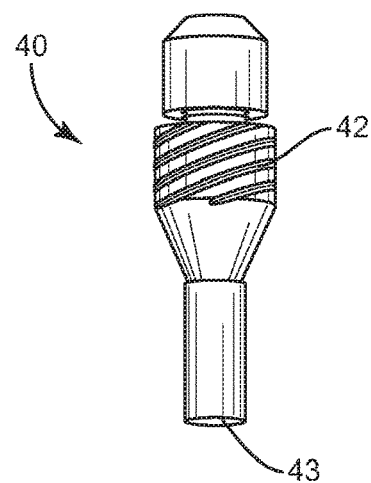
FIG. 21 is a side view of a portion of a proximal reamer.
Figure 22:
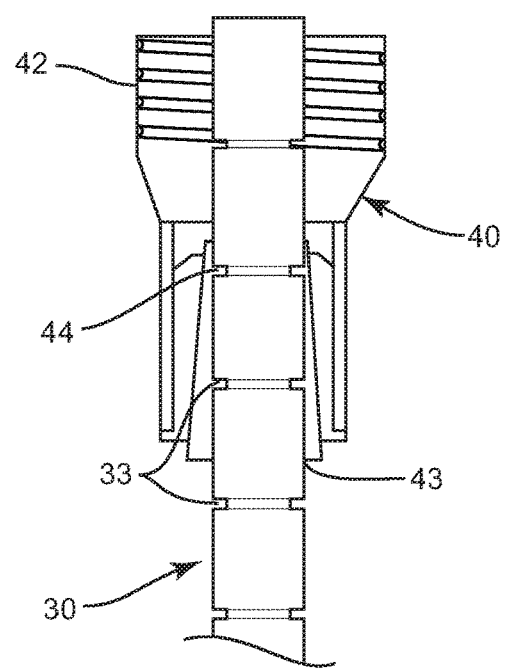
FIG. 22 is a schematic sectional side view of a distal reamer attached to a proximal reamer.

The proximal reamer 40 may lock to the distal reamer 30 in a variety of different manners. FIG. 20 illustrates a distal reamer 30 with an elongated shaft 31 and a distal cutting section 32. Notches 33 extend around the circumference of the shaft 31 and are spaced apart at set increments. As illustrated in FIG. 21, the proximal reamer 40 includes a central channel 43 that extends through the length and is sized to fit around the shaft 31 of the distal reamer 30. The exterior of the proximal reamer 40 includes a cutting section 42 configured to ream the femoral canal 103. As illustrated in FIG. 22, the central channel 43 is sized for the proximal reamer 40 to slide over the shaft 31 of the distal reamer 30. The proximal reamer 40 further includes extensions 44 that extend outward from sidewalls of the channel 43 and are sized to fit within one of the notches 33 spaced along the shaft 31.

In use, the proximal reamer 40 is inserted onto shaft 31 of the distal reamer 30 and moved along the length to the appropriate longitudinal position. The shaft 31 may include indicia at each of the notches 33 to indicate a spacing or positioning from the distal cutting section 32. The notches 33 may be positioned at 1 mm increments along an entirety of portion of the shaft 31. At the desired longitudinal position, the extensions 44 engage with the corresponding notches 33 to fix the relative positions of the reamers 30, 40.

The proximal reamer 40 may further include a locking mechanism to prevent further movement.

Figure 23:
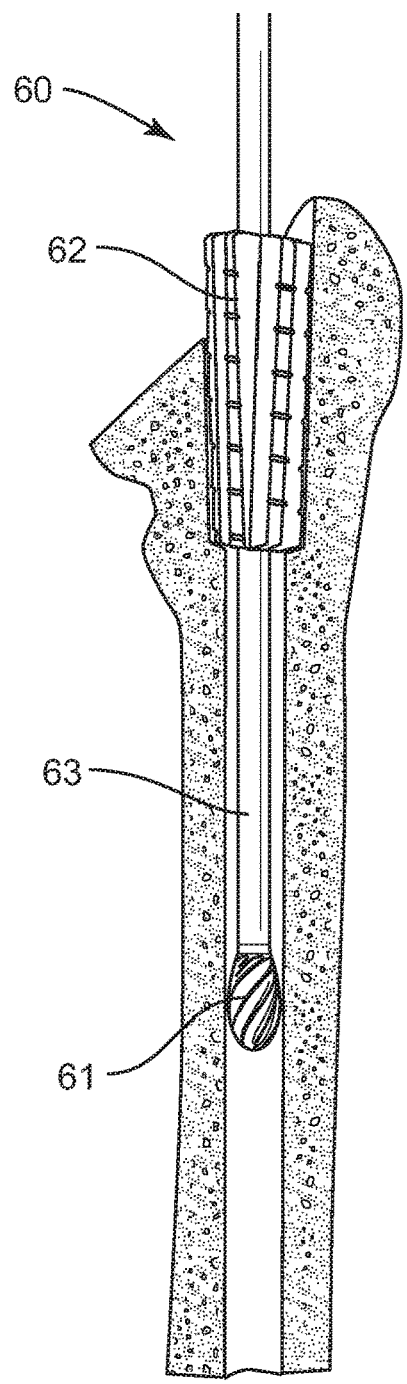
FIG. 23 is a side view of a combined reamer with proximal and distal cutting sections positioned in a femoral canal with the femur illustrated in cross section.

Another embodiment illustrated in FIG. 23 includes a combined reamer 60 with both distal and proximal cutting sections 61, 62. This reamer 60 includes a distal cutting section 61 to size the distal region 110 of the canal 103, and a proximal cutting section 62 to size the proximal region 111. An intermediate shaft 63 extends between the sections 61, 62 and may be flexible to provide for centering of the reamer 60 within the femoral canal 103. The threads on the distal and proximal sections 61, 62 may be opposite such that rotation of the reamer 60 in a first direction sizes a first section of the canal 103, and rotation in an opposing second direction sizes a second section. The specific configurations of the cutting sections 61, 62 may be the same as the sections 32, 43 described above for the reamers 30, 40.

The embodiment described above includes proximal reaming occurring during a single pass of a single proximal reamer 40. Other embodiments may include the proximal reamer 40 being passed multiple times along the proximal region 11 of the femoral canal 103. Further, different proximal reamers 40 may be used during the proximal reaming process. Likewise, reaming of the middle region 112 may include multiple passes and/or multiple mid-shaft reamers 70.

The mid-shaft reamer 70 may include a stand-alone structure as illustrated in FIG. 17. In another embodiment, the mid-shaft reamer 70 is configured to be used with the distal reamer 30. The mid-shaft reamer 70 includes a longitudinal opening sized to extend over the shaft 31 of the distal reamer 30. The mid-shaft reamer 70 is longitudinally moved along the shaft 31 and includes a cutting section 73 that reams the middle region 112 in a manner similar to that described above.

The methods and devices for the hip replacement surgery apply to any reamer-based system. It has been determined that the best results are obtained using a tapered implant, as opposed to a straight stem implant. In specific embodiments, the implant includes a 3° taper.

Figure 24:
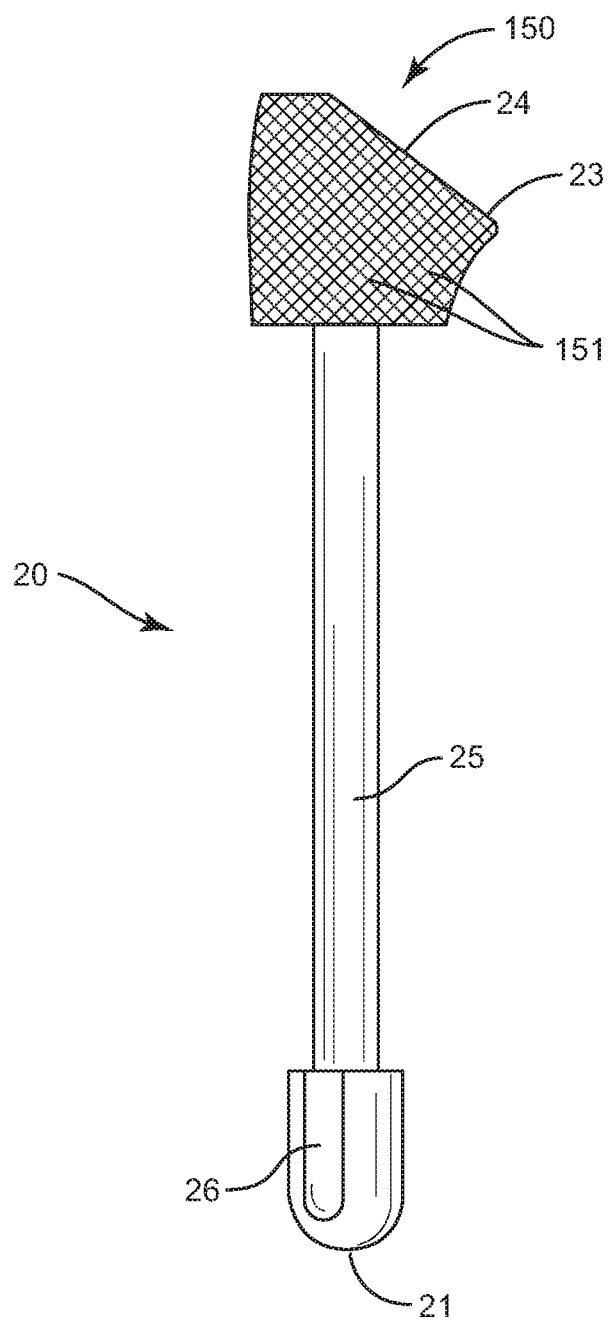
FIG. 24 is a side view of a dummy implant.

FIG. 3 illustrates one embodiment of a dummy implant 20. FIG. 24 illustrates another dummy implant 20 that includes a proximal portion 150 that mimics a rasp, such as that used for additional sizing of the canal 103 prior to insertion of the femoral component 11 and illustrated in FIG. 19. The dimensions of the proximal portion 150 correspond to the initial proximal section 144 of the cutting section 142. In one embodiment, the proximal portion 150 of the dummy implant 20 mimics about the first 1-3 cm of the proximal section 144. In a more specific embodiment, the proximal portion 150 mimics about the first 1.5 cm of the proximal section 144. In another embodiment, the proximal portion 150 includes teeth 143 and mimics the dimensions of the proximal section of the femoral component 11

The top surface of the proximal portion 150 forms the plate 23 as described above and may further include one or more openings 24. As further illustrated in FIG. 24, a remainder of the dummy implant 20 includes a shaft 25 and distal body 26.

The proximal portion 150 may include various shapes and sizes. In one embodiment, the proximal portion mimics the shape of the rasp used for sizing of the canal 103. In a specific embodiment, the proximal portion 150 has a length of about 1.5 cm that mimics the shape and size of the rasp.

Aspects of a total hip arthroplasty are disclosed in the article "The Rottinger approach for total hip arthroplasty: technique and review of the literature" by Benjamin J. Hansen, Rhett K. Hallows, and Scott S. Kelley, *Curr. Rev*

*Musculoskelet. Med.* (2011) 4:132-138. This article is herein incorporated by reference in its entirety.

The various implants and insertion tools may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of positioning a dummy implant relative to a greater trochanter of a femur to size the femur to receive a femoral component implant during a hip replacement surgical procedure, the method comprising:
   providing a dummy implant comprising a footplate at a proximal end with a cross-sectional size that replicates a proximal portion of the femoral component implant, a distal section with a cross-sectional size that replicates a distal portion of the femoral component implant, and an intermediate shaft that extends between the footplate and the distal section with a smaller cross-sectional size than an intermediate portion of the femoral component implant, the footplate extending radially outwardly beyond the shaft and the distal section having a distal end;
   inserting the dummy implant into a femoral canal of the femur and contacting the distal section of the dummy implant against a wall of the femoral canal with the shaft extending along the femoral canal and being spaced away from the wall of the femoral canal and with the footplate of the dummy implant below a superior end of the greater trochanter and contacting against a proximal end of the femur;
   determining an expected position of the femoral component implant relative to the femur based on visually observing a position of the footplate relative to the proximal end of the femur;
   using the footplate as a cutting guide and moving a blade along a top edge of the footplate and cutting a portion of the femur that extends beyond the top edge of the footplate;
   removing the dummy implant from the femoral canal; and
   inserting the femoral component implant into the femoral canal.

2. The method of claim 1, further comprising inserting the dummy implant into the femoral canal and positioning an opening in the proximal end of the footplate of the dummy implant below the greater trochanter.

3. The method of claim 1, further comprising applying a force to the dummy implant and penetrating a cutting edge on the footplate into the femur and cutting both a surface of the proximal femur and the greater trochanter.

4. The method of claim 1, further comprising visually observing the relative positioning of the footplate and the proximal femur and positioning the footplate within the outer perimeter of the proximal femur.

5. The method of claim 1, further comprising opening the femoral canal medial to the greater trochanter prior to inserting the dummy implant into the femoral canal.

6. A method of positioning a dummy implant relative to a greater trochanter of a femur to size the femur to receive a femoral component implant during a hip replacement surgical procedure, the method comprising:
   providing a dummy implant comprising a footplate at a proximal end with a cross-sectional size that replicates a proximal portion of the femoral component implant, a distal section with a cross-sectional size that replicates a distal portion of the femoral component implant, and an intermediate shaft that extends between the footplate and the distal section with a smaller cross-sectional size than an intermediate portion of the femoral component implant;
   opening a femoral canal of the femur medial to the greater trochanter;
   after opening the femoral canal, inserting the dummy implant into the femoral canal and contacting the distal section of the dummy implant against a wall of the femoral canal and with the shaft extending along the femoral canal and being spaced away from the wall of the femoral canal, and positioning a proximal end of the dummy implant below a superior end of the greater trochanter and contacting the footplate of the dummy implant against a proximal end of the femur;
   visually observing the footplate relative to the proximal end of the femur and visually determining an expected position of the femoral component implant relative to the femur;
   using the footplate as a cutting guide and moving a blade along a top edge of the footplate and cutting a portion of the femur that extends beyond the top edge of the footplate;
   removing the dummy implant from the femoral canal; and
   inserting the femoral component implant into the femoral canal and positioning the femoral component implant at the expected position.

7. The method of claim 6, further comprising inserting the dummy implant into the femoral canal and positioning an opening in the proximal end of the footplate of the dummy implant below the greater trochanter.

8. The method of claim 7, further comprising positioning the dummy implant with the opening in the proximal end of the footplate being exposed.

9. The method of claim 6, further comprising applying a force to the dummy implant and penetrating a cutting edge on the footplate into the femur and cutting both a surface of the proximal femur and the greater trochanter.

10. The method of claim 6, further comprising visually observing the relative positioning of the footplate and the proximal femur and positioning the footplate within the outer perimeter of the proximal femur.

* * * * *